(12) United States Patent
Boykin et al.

(10) Patent No.: US 7,432,278 B2
(45) Date of Patent: Oct. 7, 2008

(54) DICATIONIC IMIDAZO[1,2-A]PYRIDINES AND 5,6,7,8-TETRAHYDRO-IMIDAZO[1,2-A] PYRIDINES AS ANTIPROTOZOAL AGENTS

(75) Inventors: David W. Boykin, Atlanta, GA (US); Richard R. Tidwell, Pittsboro, NC (US); W. David Wilson, Atlanta, GA (US); Mohamed A. Ismail, Talkha (EG)

(73) Assignees: The University of North Carolina at Chapel Hill, Chapel Hill, NC (US); Georgia State University Research Foundation, Inc., Atlanta, GA (US)

( * ) Notice: Subject to any disclaimer, the term of this patent is extended or adjusted under 35 U.S.C. 154(b) by 379 days.

(21) Appl. No.: 11/074,565

(22) Filed: Mar. 8, 2005

(65) Prior Publication Data

US 2005/0282853 A1    Dec. 22, 2005

Related U.S. Application Data

(60) Provisional application No. 60/551,091, filed on Mar. 8, 2004.

(51) Int. Cl.
| | |
|---|---|
| C07D 471/02 | (2006.01) |
| C07D 491/02 | (2006.01) |
| C07D 498/02 | (2006.01) |
| C07D 513/02 | (2006.01) |
| C07D 515/02 | (2006.01) |
| A01N 43/42 | (2006.01) |
| A61K 31/44 | (2006.01) |

(52) U.S. Cl. ..................... 514/300; 546/121
(58) Field of Classification Search ................ 546/121, 546/300; 514/300
See application file for complete search history.

(56) References Cited

U.S. PATENT DOCUMENTS 5,204,352 A * 4/1993 Sundberg et al. ......... 514/259.1

FOREIGN PATENT DOCUMENTS

WO   WO 96/40138   12/1996

WO   WO 2005/025565   3/2005

OTHER PUBLICATIONS

Dann et al., Justus Liebigs Annalen der Chemie, 1972, vol. 760, pp. 37-87.*

Tidwell et al., Journal of Medicinal Chemistry. 1978, vol. 21, pp. 613-623.*

Geratz et al., Thrombosis and Haemostasis, 1978, vol. 39, pp. 411-425.*

Ismail et al., Journal of medicinal Chemistry, 2004, vol. 47, pp. 3658-3664.*

Notification Concerning Transmittal of International Preliminary Report on Patentability (Chapter I of the Patent Cooperation Treaty) corresponding to PCT International Application No. PCT/US05/07566 dated Sep. 21, 2006.

ISR and Written Opinion corresponding to PCT International Application No. PCT/US05/07566 dated Oct. 24, 2005.

Oleink et al. "Study in the arylufuran series" CA 92:180892, 1980. Abstract.

Nakatsuka et al. "Organic electroluminescent device", CA 134:70632, 2001. Abstract.

Official Action corresponding to Chinese Patent Application No. 200580007324.7 dated Mar. 21, 2008.

* cited by examiner

*Primary Examiner*—D. Margaret Seaman
*Assistant Examiner*—Niloofar Rahmani
(74) *Attorney, Agent, or Firm*—Jenkins, Wilson, Taylor & Hunt, P.A.

(57) ABSTRACT

A method for treating a microbial infection, including an infection from a protozoan pathogen, such as *Trypanosoma brucei rhodesiense* and *Plasmodium falciparum*, in a subject in need thereof by administering to the subject an effective amount of a dicationic imidazopyridine compound or a dicationic tetrahydro-imidazopyridine compound. Processes for synthesizing dicationic imidazopyridines and dicationic tetrahydro-imidazopyridines and the novel dicationic imidazopyridine and dicationic tetrahydro-imidazopyridine compounds themselves.

40 Claims, No Drawings

DICATIONIC IMIDAZO[1,2-A]PYRIDINES AND 5,6,7,8-TETRAHYDRO-IMIDAZO[1,2-A] PYRIDINES AS ANTIPROTOZOAL AGENTS

CROSS REFERENCE TO RELATED APPLICATIONS

This application claims the benefit of and priority to U.S. Provisional Patent Application Ser. No. 60/551,091, filed Mar. 8, 2004, the disclosure of which is incorporated herein by reference in its entirety.

TECHNICAL FIELD

The presently disclosed subject matter relates to methods for combating microbial infections with novel dicationic compounds, processes for synthesizing novel dicationic compounds, and the novel dicationic compounds themselves. More particularly, the presently disclosed subject matter relates to methods for combating microbial infections with dicationic imidazopyridines and dicationic tetrahydro-imidazopyridines, processes for synthesizing dicationic imidazopyridines and dicationic tetrahydro-imidazopyridines, and the novel dicationic imidazopyridine and dicationic tetrahydro-imidazopyridine compounds themselves.

| ABBREVIATIONS | |
|---|---|
| δ = | chemical shift |
| Ac = | acetyl |
| AcO = | acetoxyl |
| AcOH = | acetic acid |
| Ac$_2$O = | acetic anhydride |
| Am = | amidine |
| AmOH = | amidoxime |
| Bu = | butyl |
| ° C. = | degrees Celsius |
| calcd = | calculated |
| cm = | centimeters |
| Cs$_2$CO$_3$ = | cesium carbonate |
| dec = | decomposition point |
| DIBAL = | diisobutylaluminium hydride |
| DMF = | dimethylformamide |
| DMSO = | dimethylsulfoxide |
| D$_2$O = | deuterium oxide |
| EtOAc = | ethyl acetate |
| EtOH = | ethanol |
| g = | grams |
| h = | hours |
| HAT = | human African trypanosomiasis |
| HCl = | hydrogen chloride |
| HPLC = | high-pressure liquid chromatography |
| Hz = | hertz |
| ip = | intraperitoneal |
| kg = | kilograms |
| KO-t-Bu = | potassium tert-butoxide |
| L. d. = | Leishmania donovani |
| M = | molar |
| Me = | methyl |
| MeO = | methoxyl |
| MHz = | megahertz |
| mL = | milliliters |
| mm = | millimeters |
| mM = | millimolar |
| m.p. = | melting point |
| MS = | mass spectroscopy |
| Na$_2$CO$_3$ = | sodium carbonate |
| Na$_2$SO$_4$ = | sodium sulfate |
| NBS = | N-bromosuccinimide |
| NH$_2$OH•HCl = | hydroxylamine hydrochloride |
| NMR = | nuclear magnetic resonance |
| p = | para |
| Pd—C = | 10% palladium on carbon |
| Pd(PPh$_3$)$_4$ = | tetrakis(triphenylphosphine)palladium |
| P. f. = | Plasmodium falciparum |
| po = | oral |
| psi = | pounds per square inch |
| spp. = | species |
| T. br. = | Trypanosoma brucei rhodesiense |
| T. cruzi = | Trypanosoma cruzi |
| THF = | tetrahydrofuran |
| TLC = | thin-layer chromatography |
| TMS = | trimethylsilyl |
| UV = | ultraviolet |

BACKGROUND

The incidence of microbial infections (e.g., mycobacterial, fungal, and protozoal infections) in the immunocompromised population has significantly increased over the past several years. In particular, Candida species, especially Candida albicans, are often significant pathogens in patients infected with human immunodeficiency virus (HIV). Another pathogen, Pneumocystis carinii, causes a form of pneumonia (PCP) that is believed to be one of the leading causes of death in patients suffering from AIDS.

In addition, human African trypanosomiasis (HAT) has reemerged as a threat to over 60 million people. Current estimates are that between 350,000 and 450,000 people are infected with HAT. Other severe and life-threatening microbial infections are caused by Plasmodium spp., Mycobacterium tuberculosis, Aspergillus spp., Cryptosporidium parvum, Giardia lamblia, Toxoplasma gondii, Fusarium solani, and Cryptococcus neoformans.

The antimicrobial properties of dicationic molecules have been studied since the 1930's. Compounds of this type have typically utilized amidine groups as the cationic moieties, and their activities against a number of pathogens including Trypanosoma spp., Plasmodium spp., Cryptosporidium parvum, Giardia lamblia, Leishmania spp., Pneumocystis carinii, Toxoplasma gondii, Candida albicans, Aspergillus spp. and Cryptococcus neoformans have been reported. See, e.g., King, H., et al., Ann. Trop. Med. Parasitol., 32, 177-192 (1938); Blagburn, B. L., et al., Antimicrob. Agents Chemother., 35, 1520-1523 (1991); Bell, C. A., et al., Antimicrob. Agents Chemother., 35, 1099-1107 (1991); Bell, C. A., et al., Antimicrob. Agents Chemother., 34, 1381-1386 (1990); Kirk, R., et al., Ann. Trop. Med. Parastiol., 34, 181-197 (1940); Fulton, J. D., Ann. Trop. Med. Parasitol., 34, 53-66 (1940); Ivady. V. G., et al., Monatschr. Kinderheilkd., 106, 10-14 (1958); Boykin, D. W., et al., J. Med. Chem., 38, 912-916 (1995); Boykin, D. W., et al., J. Med. Chem., 41, 124-129 (1998); Francesconi, I., et al., J. Med. Chem., 42, 2260-2265 (1999); Lindsay, D. S., et al., Antimicrob. Agents Chemother., 35, 1914-1916 (1991); Lourie, E. M., et al., Ann. Trop. Med. Parasitol., 33, 289-304 (1939); Lourie, E. M., et al., Ann. Trop. Med. Parasitol., 33, 305-312 (1939); Das, B. P., et al., J. Med. Chem., 20, 531-536 (1976); Del Poeta, M., et al., J. Antimicrob. Chemother., 44, 223-228 (1999); Del Poeta, M., et al., Antimicrob. Agents Chemother., 42, 2495-2502 (1998); Del Poeta, M., et al., Antimicrob. Agents Chemother., 42, 2503-2510 (1998).

Despite the broad-spectrum of antimicrobial activity exhibited by aromatic diamidines, only one compound of this chemical type, pentamidine, has seen significant clinical use in humans. See Tidwell R. R. and Boykin D. W., Dicationic DNA Minor Groove Binders as Antimicrobial Agents, in *Small Molecule DNA and RNA Binders: From Synthesis to Nucleic Acid Complexes*, (Demeunynck, M.; Bailly, C. and Wilson, W. D. (eds.) Wiley-VCH, New York), Vol. 2, pp 414-460 (2003). Pentamidine has been used clinically against African trypanosomiasis, antimony-resistant leishmaniasis, and *P. carinii* pneumonia. See, e.g., Apted, F. I. C., *Pharmacol. Ther.*, 11, 391-413 (1980); Bryceson, A. D. M., et al., *Trans. Roy. Soc. Trop. Med. Hyg.*, 79, 705-714 (1985); Hughes, W. T., et al., *Antimicrob. Agents Chemother.*, 5, 289-293 (1974). Thus, there continues to be a need for improvement in the art for additional compounds having desirable antimicrobial activity, whether against the representative pathogens referenced above or against other pathogens.

SUMMARY

In some embodiments, the presently disclosed subject matter provides a compound of Formula (I):

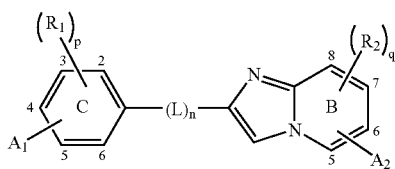

wherein:
n is an integer from 0 to 1;
p is an integer from 0 to 4;
q is an integer from 0 to 3;
L is selected from the group consisting of

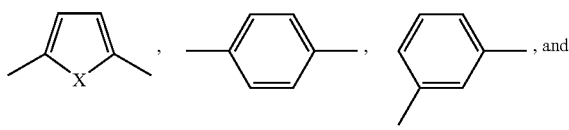

wherein X is selected from the group consisting of O, S, and $NR_3$, and wherein $R_3$ is selected from the group consisting of H, alkyl, substituted alkyl, and alkoxyl;

$R_1$ and $R_2$ are each independently selected from the group consisting of alkyl, substituted alkyl, aryl, substituted aryl, halo, hydroxyl, alkoxyl, aryloxyl, and aralkyloxyl.

B is selected from the group consisting of a saturated ring structure, a partially saturated ring structure, and an unsaturated ring structure;

$A_1$ and $A_2$ are each independently selected from the group consisting of:

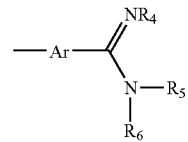

wherein:
Ar is selected from the group consisting of an aryl group and a substituted aryl group and can be present or absent;
$R_4$, $R_5$, and $R_6$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_4$ and $R_5$ together represent a $C_2$ to $C_{10}$ alkyl, hydroxyalkyl, or alkylene.

In some embodiments, the presently disclosed subject matter provides pharmaceutical formulations comprising a compound of Formula (I) in a pharmaceutically acceptable carrier.

In some embodiments, the presently disclosed subject matter provides a method for treating a microbial infection, including infections from protozoan pathogens, such as *Trypanosoma brucei rhodesiense* and *Plasmodium falciparum*, in a subject in need thereof. In some embodiments, the method comprises administering to the subject an effective amount of a compound of Formula (I).

In some embodiments, the presently disclosed subject matter provides the use of an active compound as described hereinabove, i.e., a compound of Formula (I), for the preparation of a medicament for treating a microbial infection.

In some embodiments, the presently disclosed subject matter provides a method for preparing a compound of Formula (I).

It is accordingly an aspect of the presently disclosed subject matter to provide compounds that are useful in the treatment of microbial infections. It is another aspect of the presently disclosed subject matter to provide pharmaceutical formulations for use in the treatment of microbial infections. It is another aspect of the presently disclosed subject matter to provide a method for treating a microbial infection. It is another aspect of the presently disclosed subject matter to provide a process for synthesizing compounds that are useful in the treatment of a microbial infection.

Certain aspects of the presently disclosed subject matter having been stated hereinabove, which are addressed in whole or in part by the presently disclosed subject matter, other aspects will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

Referring now to Scheme 1, 2,5-Bis[4-(methoxyamidino) phenyl]furan (Compound IIIa), a prodrug of furamidine, [2,5-Bis(4-amidinophenyl)furan] (Compound IIa), is an effective anti-trypanosomal compound that is currently entered into Phase II clinical trials as an oral drug versus human African trypanosomiasis. See Tidwell R. R. and Boykin D. W., Dicationic DNA Minor Groove Binders as Antimicrobial Agents, in *Small Molecule DNA and RNA Binders: From Synthesis to Nucleic Acid Complexes*, (Demeunynck, M.; Bailly, C. and Wilson, W. D. (eds.) Wiley-VCH, New York), Vol. 2, pp 414-460 (2003). Recently, Ismail, M. A., et al., *J. Med. Chem.*, 46, 4761-4769 (2003), have studied alterations of the 2,5-phenyl groups of furamidine by replacing the phenyl group(s) with pyridyl group(s) (e.g., Compounds IIb and IIIb of Scheme 1). Several prodrugs of these aza-analogues show oral activity in vivo that is superior to that of the respective parent furamidines.

Sheme 1.
Representative biologically active aromatic diamidines.

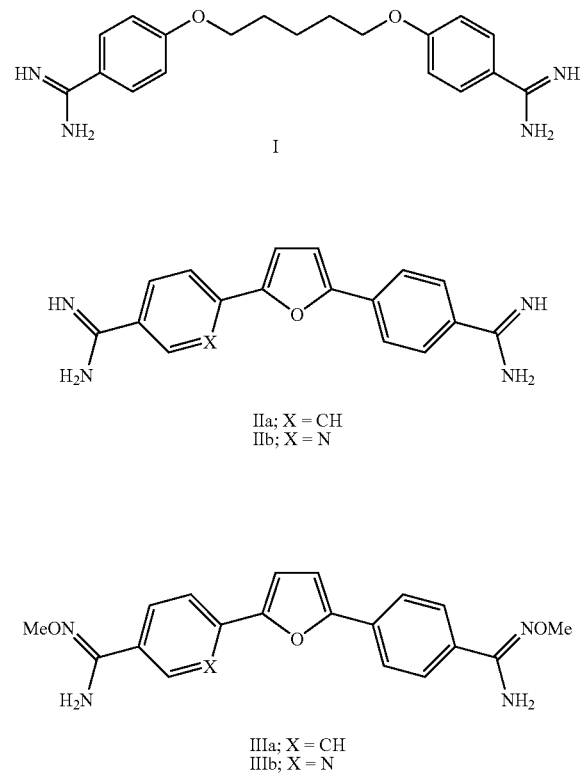

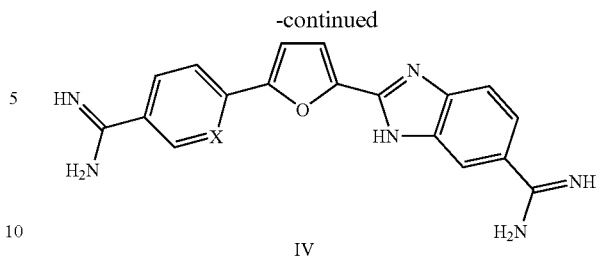

IV

These biologically active aromatic diamidines bind the minor groove of DNA at AT rich sites. Boykin, D. W., et al., *J. Med. Chem.*, 38, 912-916 (1995); Boykin, D. W., et al., *J. Med. Chem.*, 41, 124-129 (1998); Francesconi, I., et al., *J. Med. Chem.*, 42, 2260-2265 (1999); Czarny, A. et al., *J. Am. Chem. Soc.*, 117, 4716-4717 (1995); Laughton, C. A., et al., *Biochemistry*, 35, 5655-5661 (1996); Trent, J. O., et al., *J. Med. Chem.*, 39, 4554-4562 (1996); Wilson, W. D., et al. *J. Am. Chem. Soc.*, 120, 10310-10321 (1998). Without being limited to any one particular theory, it is thought that the minor groove binding leads to inhibition of one or more DNA dependant enzymes, which gives rise to the antimicrobial effect. Bailly, C., et al., *Anti-Cancer Drug Design*, 14, 47-60 (1999); Fitzgerald, D. J., et al., *J. Biol. Chem.*, 274, 27128-27138 (1999); Dykstra, C. C., et al., *Antimicrob. Agents Chemother.*, 38, 1890-1898 (1994).

Further, a number of effective aromatic diamidines include one or more benzimidazole units as part of the aromatic framework. Tidwell, R. R., et al., *J. Med. Chem.*, 21, 613-23 (1978); Del Poeta M., et al., *Antimicrobial Agents and Chemotherapy*, 42, 2495-2502 (1998); Del Poeta M., et al., *Antimicrobial Agents and Chemotherapy*, 42, 2503-2509 (1998); Lombardy, R., et al., *J. Med. Chem.*, 39, 1442-1462 (1996). One of these benzimidazole analogues, compound IV of Scheme 1, has been found to bind DNA in an unusual stacked dimer array, which offers the potential for the development of new gene regulation molecules. Wang, L., et al., *Proc. Natl. Acad. USA*, 97, 12-16 (2000); Hopkins, K., et al., *J. Med. Chem.*, 41, 3872-3878 (1998); Wang, L., et al., *Biochemistry*, 40, 2511-2521 (2001); Bailly, C., et al., *Biochemistry*, 40, 9770-9779 (2001).

In some embodiments, the presently disclosed subject matter provides compounds in which the benzimidazole group in the aromatic diamidine is replaced with an imidazo[1,2-a] pyridine or a 5,6,7,8-tetrahydro-imidazo[1,2-a]pyridine. Without being bound to any one particular theory, such alterations in structure offer the potential to change the base pair recognition on DNA binding and to yield different absorption and distribution profiles.

In some embodiments, the presently disclosed subject matter also provides the synthesis of novel diamidino imidazo[1,2-a]pyridines and 5,6,7,8-tetrahydro-imidazo[1,2-a]pyridines and their corresponding N-hydroxy and N-methoxy analogues, which are potential prodrugs for this series. Further, in some embodiments, the presently described subject matter demonstrates the biological activity of the presently disclosed novel diamidino imidazo[1,2-a]pyridines and 5,6,7,8-tetrahydro-imidazo[1,2-a]pyridines and their corresponding N-hydroxy and N-methoxy analogues versus *Trypanosoma b. rhodesiense* (T. b. r.) and *Plasmodium falciparum* (P. f.).

I. Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by the formula:

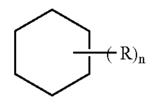

as used herein refers to a ring structure, for example, but not limited to a 3-carbon, a 4-carbon, a 5-carbon, a 6-carbon, and the like, aliphatic and/or aromatic cyclic compound, including a saturated ring structure, a partially saturated ring structure, and an unsaturated ring structure as defined herein, comprising a substituent R group, wherein the R group can be present or absent, and when present, one or more R groups can each be substituted on one or more available carbon atoms of the ring structure. The presence or absence of the R group and number of R groups is determined by the value of the integer n.

Each R group, if more than one, is substituted on an available carbon of the ring structure rather than on another R group. For example, the structure above where n is 0 to 2 would comprise compound groups including, but not limited to:

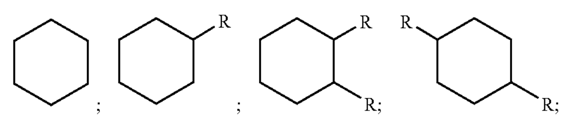

and the like.

A dashed line representing a bond in a cyclic ring structure indicates that the bond can be either present or absent in the ring. That is a dashed line representing a bond in a cyclic ring structure indicates that the ring structure is selected from the group consisting of a saturated ring structure, a partially saturated ring structure, and an unsaturated ring structure.

In some embodiments, the compounds described by the presently disclosed subject matter contain a linking group. As used herein, the term "linking group" comprises a chemical moity, such as a furanyl, phenylene, thienyl, and pyrrolyl radical, which is bonded to two or more other chemical moieties, in particular aryl groups, to form a stable structure.

When a named atom of an aromatic ring or a heterocyclic aromatic ring is defined as being "absent," the named atom is replaced by a direct bond. When the linking group or spacer group or "Ar" group is defined as being absent, the linking group or spacer group or "Ar" group is replaced by a direct bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" or "alkoxyalkyl" refer to an alkyl-O— group wherein alkyl is as previously described. The term "alkoxyl" as used herein can refer to C$_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an H$_2$N—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

The term "amino" refers to the —NH$_2$ group.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

When the term "independently selected" is used, the substituents being referred to (e.g., R groups, such as groups R$_1$ and R$_2$, or groups X and Y), can be identical or different. For example, both R$_1$ and R$_2$ can be substituted alkyls, or R$_1$ can be hydrogen and R$_2$ can be a substituted alkyl, and the like.

A named "R", "R'," "X," "Y," "Y'," "A," "A'," "B," "L," or "Z" group will generally have the structure that is recognized in the art as corresponding to a group having that name, unless specified otherwise herein. For the purposes of illustration, certain representative "R," "X," "Y", and "A" groups as set forth above are defined below. These definitions are intended to supplement and illustrate, not preclude, the definitions that would be apparent to one of ordinary skill in the art upon review of the present disclosure.

The term "reflux" and grammatical derivations thereof refer to boiling a liquid, such as a solvent, in a container, such as a reaction flask, with which a condenser is associated, thereby facilitating continuous boiling without loss of liquid, due to the condensation of vapors on the interior walls of the condenser.

The term "aprotic solvent" refers to a solvent molecule which can neither accept nor donate a proton. Typical aprotic solvents include, but are not limited to, acetone, acetonitrile, benzene, butanone, butyronitrile, carbon tetrachloride, chlorobenzene, chloroform, 1,2-dichloroethane, dichloromethane, diethyl ether, dimethylacetamide, N,N-dimethylformamide (DMF), dimethylsulfoxide (DMSO), 1,4-dioxane, ethyl acetate, ethylene glycol dimethyl ether, hexane, N-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents. Examples of nonpolar, aprotic solvents include, but are not limited to, diethyl ether, aliphatic hydrocarbons, such as hexane, aromatic hydrocarbons, such as benzene and toluene, and symmetrical halogenated hydrocarbons, such as carbon tetrachloride.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

The term "metal alkyl" refers to a compound of the general formula $MR_n$, wherein M is a metal atom, including, but not limited to aluminum, boron, magnesium, zinc, gallium, indium, antimony and related metals, R is an alkyl group as defined herein, and n is an integer. A representative metal alkyl is trimethylaluminum, abbreviated as $Al(CH_3)_3$ or $AlMe_3$.

The term "alkali metal alcoholate" refers to an alkali metal derivative of an alcohol having the general formula $M_aOR_n$, wherein $M_a$ is an alkali metal, such as lithium, sodium, or potassium, O is oxygen, R is an alkyl group as defined herein, and n is an integer. Representative alkali metal alcoholates include, but are not limited to, sodium methanolate, abbreviated as $NaOCH_3$ or NaOMe, and potassium butoxide, abbreviated as $KOC(CH_3)_3$.

The term "acid anhydride" refers to an anhydride of an organic acid and includes, but is not limited to acetic anhydride (($CH_3C{=}O)_2O$ or $Ac_2O$) and benzoic anhydride (($C_6H_5C{=}O)_2O$).

II. Novel Compounds
  II.A. Compounds of Formula (I)
  Described herein is a compound of Formula (I):

wherein:
  n is an integer from 0 to 1;
  p is an integer from 0 to 4;
  q is an integer from 0 to 3;
  $R_1$ and $R_2$ are each independently selected from the group consisting of alkyl, substituted alkyl, aryl, substituted aryl, halo, hydroxyl, alkoxyl, aryloxyl, and aralkyloxyl;
  L is selected from the group consisting of wherein X is selected from the group consisting of O, S, and $NR_3$, and wherein $R_3$ is selected from the group consisting of H, alkyl, substituted alkyl, and alkoxyl;
  B is selected from the group consisting of a saturated ring structure, a partially saturated ring structure, and an unsaturated ring structure;
  $A_1$ and $A_2$ are each independently:

wherein:
  Ar is selected from the group consisting of an aryl group and a substituted aryl group and can be present or absent;
  $R_4$, $R_5$, and $R_6$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
  $R_4$ and $R_5$ together represent a $C_2$ to $C_{10}$ alkyl, hydroxyalkyl, or alkylene;

or a pharmaceutically acceptable salt thereof.

In some embodiments, n is 1 and L comprises a 2,5-furanyl radical, wherein X is oxygen. In some embodiments, n is 1 and L comprises a 1,3-phenylene radical. In some embodiments, n is 1 and L comprises a 1,4-phenylene radical. In some embodiments, n is 0.

In some embodiments, B is a saturated ring structure. In some embodiments, B is a partially saturated ring structure. In some embodiments, B is an unsaturated ring structure.

In some embodiments, $R_2$ is alkyl. In some embodiments, $R_2$ is a methyl group.

In some embodiments, $A_1$ and $A_2$ are both wherein $R_5$ and $R_6$ are H, and $R_4$ is selected from the group consisting of H, hydroxyl, and alkoxyl. In some embodiments, $R_4$ is H. In some embodiments, $R_4$ is hydroxyl. In some embodiments, $R_4$ is alkoxyl. In some embodiments, $R_4$ is methoxyl.

In some embodiments, $A_1$ comprises and $A_2$ comprises

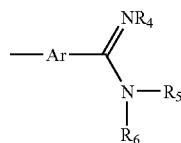

wherein Ar is selected from the group consisting of an aryl group and a substituted aryl group, $R_5$ and $R_6$ are H, and $R_4$ is selected from the group consisting of H, hydroxyl, and alkoxyl. In some embodiments, the aryl group comprises a phenylene radical. In some embodiments, $R_4$ is H. In some embodiments, $R_4$ is hydroxyl. In some embodiments, $R_4$ is alkoxyl. In some embodiments, $R_4$ is methoxyl.

In some embodiments, the $A_1$ group is in the 4-position of ring C. In some embodiments, the $A_2$ group is in the 6-position of ring B.

In some embodiments, the compound of Formula (I) is selected from the group consisting of: N-Hydroxy-2-{5-[4-(N-hydroxyamidino)-phenyl]-furan-2-yl}-imidazo[1,2-a]pyridine-6-carboxamidine (5a); N-Methoxy-2-{5-[4-(N-methoxyamidino)-phenyl]-furan-2-yl}-imidazo[1,2-a]pyridine-6-carboxamidine (6); 2-[5-(4-Amidinophenyl)-furan-2-yl]-5,6,7,8-tetrahydro-imidazo[1,2-a]pyridine-6-carboxamidine (7); 2-[5-(4-Amidinophenyl)-furan-2-yl]-imidazo[1,2-a]pyridine-6-carboxamidine (8a); N-Hydroxy-2-{5-[4-(N-hydroxyamidino)-phenyl]-furan-2-yl}-8-methyl-imidazo[1,2-a]pyridine-6-carboxamidine (5b); 2-[5-(4-Amidinophenyl)-furan-2-yl]-8-methyl-imidazo[1,2-a]pyridine-6-carboxamidine (8b); N-Hydroxy-2-[4'-(N-hydroxyamidino)-biphenyl-4-yl]-imidazo[1,2-a]pyridine-6-carboxamidine (11a); N-Methoxy-2-[4'-(N-methoxyamidino)-biphenyl-4-yl]-imidazo[1,2-a]pyridine-6-carboxamidine (12); 2-(4'-Amidinobiphenyl-4-yl)-5,6,7,8-tetrahydro-imidazo[1,2-a]pyridine-6-carboxamidine (13a); 2-(4'-Amidinobiphenyl-4-yl)-imidazo[1,2-a]pyridine-6-carboxamidine (14a); N-Hydroxy-2-[4'-(N-hydroxyamidino)-biphenyl-3-yl]-imidazo[1,2-a]pyridine-6-carboxamidine (11b); 2-(4'-Amidinobiphenyl-3-yl)-5,6,7,8-tetrahydro-imidazo[1,2-a]pyridine-6-carboxamidine (13b); 2-(4'-Amidinobiphenyl-3-yl)-imidazo[1,2-a]pyridine-6-carboxamidine (14b); N-Hydroxy-2-[4'-(N-hydroxyamidino)-biphenyl-3-yl]-8-methyl-imidazo[1,2-a]pyridine-6-carboxamidine (11c); 2-(4'-Amidinobiphenyl-3-yl)-8-methyl-imidazo[1,2-a]pyridine-6-carboxamidine (14c); 2,6-Bis[4-(N-hydroxyamidino-phenyl)]-imidazo[1,2-a]pyridine (17); 2,6-Bis[4-amidinophenyl)]-5,6,7,8-tetrahydro-imidazo[1,2-a]pyridine (18); 2,6-Bis[amidinophenyl)]-imidazo[1,2-a]pyridine (19); 2,6-Bis[4-(N-hydroxyamidino-phenyl)]-8-methyl-imidazo[1,2-a]pyridine (22); and 2,6-Bis[4-amidinophenyl)]-8-methyl-imidazo[1,2-a]pyridine (23), or a pharmaceutically acceptable salt thereof.

In some embodiments, the compound of Formula I comprises a pharmaceutically acceptable salt. In some embodiments, the pharmaceutically acceptable salt comprises a hydrochloride salt. In some embodiments, the pharmaceutically acceptable salt comprises an acetate salt.

II.B. Prodrugs

In representative embodiments, compounds disclosed herein are prodrugs. A prodrug means a compound that, upon administration to a recipient, is capable of providing (directly or indirectly) a compound of the presently disclosed subject matter or an inhibitorily active metabolite or residue thereof. Prodrugs can increase the bioavailability of the compounds of the presently disclosed subject matter when such compounds are administered to a subject (e.g., by allowing an orally administered compound to be more readily absorbed into the blood) or can enhance delivery of the parent compound to a biological compartment (e.g., the brain or lymphatic system) relative to a metabolite species, for example. A number of the compounds (e.g., Compounds 5a, 5b, 6, 11a, 11b, 11c, 12, and 17) disclosed herein are prodrugs.

II.C. Pharmaceutically Acceptable Salts

Additionally, the active compounds as described herein can be administered as a pharmaceutically acceptable salt. Such pharmaceutically acceptable salts include the gluconate, lactate, acetate, tartarate, citrate, phosphate, borate, nitrate, sulfate, and hydrochloride salts. The salts of the compounds described herein can be prepared, for example, by reacting two equivalents of the base compound with the desired acid in solution. After the reaction is complete, the salts are crystallized from solution by the addition of an appropriate amount of solvent in which the salt is insoluble. In some embodiments, as described in more detail herein below, the hydrochloride salt of an amidoxime compound is made by passing hydrogen chloride gas into an ethanolic solution of the free base. In some embodiments, as described in more detail herein below, the acetate salt of the presently disclosed diamidine compounds and/or the corresponding N-methoxy analogues are made directly from the appropriate N-hydroxy analogue. Accordingly, in some embodiments, the pharmaceutically acceptable salt is a hydrochloride salt. In some embodiments, the pharmaceutically acceptable salt is an acetate salt.

III. Pharmaceutical Formulations

The compounds of Formula (I), the pharmaceutically acceptable salts thereof, prodrugs corresponding to compounds of Formula (I), and the pharmaceutically acceptable salts thereof, are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral, intravenous, or aerosol administration as discussed in greater detail below. Also, the presently disclosed subject matter provides such active compounds that have been lyophilized and that can be reconstituted to form pharmaceutically acceptable formulations for administration, for example, as by intravenous or intramuscular injection.

The therapeutically effective dosage of any specific active compound, the use of which is within the scope of embodiments described herein, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day fora period of two to three weeks or until the condition is essentially controlled. Lower doses given less frequently can be used prophylactically to prevent or reduce the incidence of recurrence of the infection.

In accordance with the present methods, pharmaceutically active compounds as described herein can be administered orally as a solid or as a liquid, or can be administered intramuscularly or intravenously as a solution, suspension, or emulsion. Alternatively, the compounds or salts also can be administered by inhalation, intravenously, or intramuscularly as a liposomal suspension. When administered through inhalation the active compound or salt should be in the form of a plurality of solid particles or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations comprise a compound of Formula (I) described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formula (I) or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a compound of Formula (I), or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation will comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

IV. Methods for Treating Microbial Infections

Subjects with microbial infections can be treated by methods described herein. Such infections can be caused by a variety of microbes, including fungi, algae, protozoa, bacteria, and viruses. Exemplary microbial infections that can be treated by the method of the presently disclosed subject matter include, but are not limited to, infections caused by *Trypanosoma* species (e.g., *Trypanosoma brucei rhodesiense*), *Plasmodium* species (e.g., *Plasmodium falciparum*), *Mycobacterium tuberculosis*, *Pneumocytsis carnii*, *Giardia lamblia*, *Cryptosporidium parvum*, *Cryptococcus neoformans*, *Candida albicans*, *Candida tropicalis*, *Salmonella typhimurium*, *Leishmania donovani*, and *Leishmania mexicana amazonensis*. The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition.

The methods for treating microbial infections comprise administering to a subject in need of treatment thereof an active compound as described herein. These active compounds, as set forth above, include compounds of Formula (I), their corresponding prodrugs, and pharmaceutically acceptable salts of the compounds and prodrugs.

With regard to the presently described method embodiments, compounds of Formula (I) are defined as having a structure as follows:

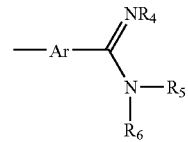

(I)

wherein:
n is an integer from 0 to 1;
p is an integer from 0 to 4;
q is an integer from 0 to 3;
$R_1$ and $R_2$ are each independently selected from the group consisting of alkyl, substituted alkyl, aryl, substituted aryl, halo, hydroxyl, alkoxyl, aryloxyl, and aralkyloxyl;
L is selected from the group consisting of

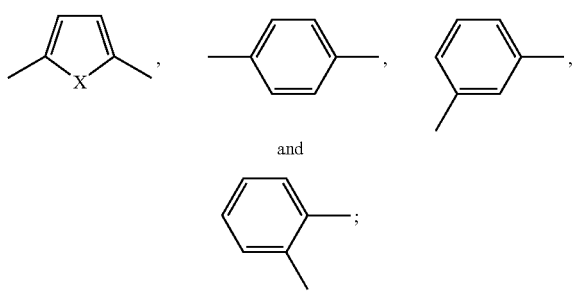

wherein X is selected from the group consisting of O, S, and $NR_3$, and wherein $R_3$ is selected from the group consisting of H, alkyl, substituted alkyl, and alkoxyl;
B is selected from the group consisting of a saturated ring structure, a partially saturated ring structure, and an unsaturated ring structure;
$A_1$ and $A_2$ are each independently:

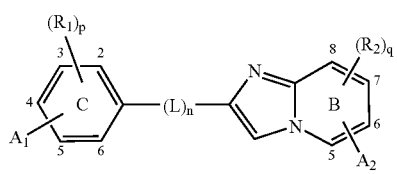

wherein:
Ar is selected from the group consisting of an aryl group and a substituted aryl group and can be present or absent;
$R_4$, $R_5$, and $R_6$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_4$ and $R_5$ together represent a $C_2$ to $C_{10}$ alkyl, hydroxyalkyl, or alkylene;

or a pharmaceutically acceptable salt thereof.

In some embodiments of the presently disclosed subject matter, n is 1 and L comprises a 2,5-furanyl radical, wherein X is oxygen. In some embodiments, n is 1 and L comprises a 1,3-phenylene radical. In some embodiments, n is 1 and L comprises a 1,4-phenylene radical. In some embodiments, n is 0 and L is absent.

In some embodiments, B is a saturated ring structure. In some embodiments, B is a partially saturated ring structure. In some embodiments, B is an unsaturated ring structure.

In some embodiments, $R_2$ is alkyl. In some embodiments, $R_2$ is a methyl group.

In some embodiments, $A_1$ and $A_2$ are

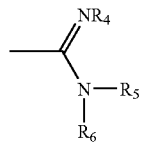

wherein $R_5$ and $R_6$ are H, and $R_4$ is selected from the group consisting of H, hydroxyl, and alkoxyl. In some embodiments, $R_4$ is H. In some embodiments, $R_4$ is hydroxyl. In some embodiments, $R_4$ is alkoxyl. In some embodiments, $R_4$ is methoxyl.

In some embodiments, $A_1$ comprises

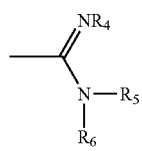

and $A_2$ comprises

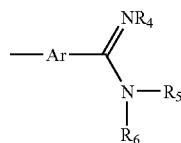

wherein Ar is selected from the group consisting of an aryl group and a substituted aryl group, $R_5$ and $R_6$ are H, and $R_4$ is selected from the group consisting of H, hydroxyl, and alkoxyl. In some embodiments, the aryl group comprises a phenylene radical. In some embodiments, $R_4$ is H. In some embodiments, $R_4$ is hydroxyl. In some embodiments, $R_4$ is alkoxyl. In some embodiments, $R_4$ is methoxyl.

In some embodiments, the $A_1$ group is in the 4-position of ring C. In some embodiments, the $A_2$ group is in the 6-position of ring B.

In some embodiments, the method comprises administering to a subject in need of therapeutic treatment a compound selected from the group consisting of: N-Hydroxy-2-{5-[4-(N-hydroxyamidino)-phenyl]-furan-2-yl}-imidazo[1,2-a]pyridine-6-carboxamidine (5a); N-Methoxy-2-{5-[4-(N-methoxyamidino)-phenyl]-furan-2-yl}-imidazo[1,2-a]pyridine-6-carboxamidine (6); 2-[5-(4-Amidinophenyl)-furan-2-yl]-5,6,7,8-tetrahydro-imidazo[1,2-a]pyridine-6-carboxamidine (7); 2-[5-(4-Amidinophenyl)-furan-2-yl]-imidazo[1,2-a]pyridine-6-carboxamidine (8a); N-Hydroxy-2-{5-[4-(N-hydroxyamidino)-phenyl]-furan-2-yl}8-methyl-imidazo[1,2-a]pyridine-6-carboxamidine (5b); 2-[5-(4-Amidinophenyl)-furan-2-yl]-8-methyl-imidazo[1,2-a]pyridine-6-carboxamidine (8b); N-Hydroxy-2-[4'-(N-hydroxyamidino)-biphenyl-4-yl]-imidazo[1,2-a]pyridine-6-carboxamidine (11a); N-Methoxy-2-[4'-(N-methoxyamidino)-biphenyl-4-yl]-imidazo[1,2-a]pyridine-6-carboxamidine (12); 2-(4'-Amidinobiphenyl-4-yl)-5,6,7,8-tetrahydro-imidazo[1,2-a]pyridine-6-carboxamidine (13a); 2-(4'-Amidinobiphenyl-4-yl)-imidazo[1,2-a]pyridine-6-carboxamidine (14a); N-Hydroxy-2-[4'-(N-hydroxyamidino)-biphenyl-3-yl]-imidazo[1,2-a]pyridine-6-carboxamidine (11b); 2-(4'-Amidinobiphenyl-3-yl)-5,6,7,8-tetrahydro-imidazo[1,2-a]pyridine-6-carboxamidine (13b); 2-(4'-Amidinobiphenyl-3-yl)-imidazo[1,2-a]pyridine-6-carboxamidine (14b); N-Hydroxy-2-[4'-(N-hydroxyamidino)-biphenyl-3-yl]-8-methyl-imidazo[1,2-a]pyridine-6-carboxamidine (11c); 2-(4'-Amidinobiphenyl-3-yl)-8-methyl-imidazo[1,2-a]pyridine-6-carboxamidine (14c); 2,6-Bis[4-(N-hydroxyamidino-phenyl)]-imidazo[1,2-a]pyridine (17); 2,6-Bis[4-amidinophenyl)]-5,6,7,8-tetrahydro-imidazo[1,2-a]pyridine (18); 2,6-Bis[amidinophenyl)]-imidazo[1,2-a]pyridine (19); 2,6-Bis[4-(N-hydroxyamidino-phenyl)]-8-methyl-imidazo[1,2-a]pyridine (22); and 2,6-Bis[4-amidinophenyl)]-8-methyl-imidazo[1,2-a]pyridine (23), or a pharmaceutically acceptable salt thereof.

In some embodiments, the compound of Formula I is administered in the form of a pharmaceutically acceptable salt. In some embodiments, the pharmaceutically acceptable salt comprises a hydrochloride salt. In some embodiments, the pharmaceutically acceptable salt comprises an acetate salt.

In some embodiments, the microbial infection is a *Trypanosoma brucei rhodesiense* infection. In some embodiments, the microbial infection is a *Plasmodium falciparum* infection.

The subject treated in the presently disclosed subject matter in its many embodiments is desirably a human subject, although it is to be understood the methods described herein are effective with respect to all vertebrate species, which are intended to be included in the term "subject." The methods described herein are particularly useful in the treatment and/or prevention of infectious diseases in warm-blooded vertebrates. Thus, the methods can be used as treatment for mammals and birds.

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

V. General Processes for the Synthesis of Diamidino Imidazo [1,2-a]pyridines and 5,6,7,8-tetrahydro-imididazo[1,2-a]pyridines of Formula (I) and Their Corresponding N-hydroxy and N-methoxy Analogues The synthetic procedures provided herein below comprise representative embodiments of novel methods of producing the presently disclosed compounds. The methods are outlined in Schemes 2-5 presented herein below and representative, non-limiting details are described in the Examples.

In some embodiments, the presently disclosed subject matter provides a method for preparing a compound of Formula (I) and pharmaceutically acceptable salts thereof, the method comprising:

(a) reacting an aryl-substituted alkylketone halide with an aminopyridine to form an aryl-substituted imidazo[1,2-a]pyridine;

(b) mixing the aryl-substituted imidazo[1,2-a]pyridine and a first catalyst in the presence of a base to form a first reaction mixture;

(c) adding a cyanophenyl-boronic acid to the first reaction mixture to form a cyanophenyl derivative of the aryl-substituted imidazo[1,2-a]pyridine;

(d) mixing an alkali metal alkoxide and a reducing agent to form a second reaction mixture; and (e) adding the second reaction mixture to the cyanophenyl derivative of the aryl-substituted imidazo[1,2-a]pyridine to form an imidazo[1,2-a]pyridine bis-amidoxime of Formula (I).

In some embodiments, the aryl-substituted alkylketone halide is selected from the group consisting of 2-Bromo-1-(5-bromo-furan-2-yl)-ethanone (2), 3-Bromophenacyl bromide, 4-Bromophenacyl bromide, and 4-Cyanophenacyl bromide. In some embodiments, the amino-pyridine is selected from the group consisting of an amino-cyanopyridine, an alkylated amino-cyanopyridine, and an amino-halopyridine. In some embodiments, the amino-cyanopyridine comprises 6-Amino-3-cyanopyridine. In some embodiments, the alkylated amino-cyanopyridine comprises 6-Amino-5-methyl-3-cyanopyridine. In some embodiments, the amino-halopyridine comprises 2-Amino-5-bromopyridine. In some embodiments, the halopyridine comprises 2-Amino-5-bromo-3-methylpyridine.

In some embodiments, the aryl-substituted imidazo[1,2-a]pyridine is selected from the group consisting of: 2-(5-Bromo-furan-2-yl)-imidazo[1,2-a]pyridine-6-carbonitrile (3a); 2-(5-Bromofuran-2-yl)-8-methyl-imidazo[1,2-a]pyridine-6-carbonitrile (3b); 2-(4-Bromophenyl)-imidazo[1,2-a]pyridine-6-carbonitrile (9a); 2-(3-Bromophenyl)-imidazo[1,2-a]pyridine-6-carbonitrile (9b); 2-(3-Bromophenyl)-8-methyl-imidazo[1,2-a]pyridine-6-carbonitrile (9c); 4-(6-Bromo-imidazo[1,2-a]pyridine-2-yl)-benzonitrile (15); and 4-(6-Bromo-8-methyl-imidazo[1,2-a]pyridin-2-yl)-benzonitrile (20).

In some embodiments, the first catalyst comprises tetrakis(triphenylphosphine)palladium. In some embodiments, the base comprises a carbonate salt. In some embodiments, the carbonate salt is selected from the group consisting of sodium carbonate and cesium carbonate. In some embodiments, the cyanophenyl-boronic acid comprises 4-Cyanophenyl boronic acid.

In some embodiments, the cyanophenyl derivative of the aryl-substituted imidazo[1,2-a]pyridine formed in step (c) immediately hereinabove is selected from the group consisting of: 2-[5-(4-Cyanophenyl)-furan-2-yl]-imidazo[1,2-a]pyridine-6-carbonitrile (4a); 2-[5-(4-Cyanophenyl)-furan-2-yl]-8-methyl-imidazo[1,2-a]pyridine-6-carbonitrile (4b); 2-(4'-Cyano-biphenyl-4-yl)-imidazo[1,2-a]pyridine-6-carbonitrile (10a); 2-(4'-Cyanobiphenyl-3-yl)-imidazo[1,2-a]pyridine-6-carbonitrile (10b); 2-(4'-Cyanobiphenyl-3-yl)-8-methyl-imidazo[1,2-a]pyridine-6-carbonitrile (10c); 2,6-Bis(4-cyanophenyl)-imidazo[1,2-a]pyridine (16); and 2,6-Bis(4-cyanophenyl)-8-methyl-imidazo[1,2-a]pyridine (21).

In some embodiments, the alkali metal alkoxide comprises potassium-t-butoxide. In some embodiments, the reducing agent comprises hydroxylamine hydrochloride.

In some embodiments, the imidazo[1,2-a]pyridine bis-amidoxime formed in step (e) immediately hereinabove is selected from the group consisting of: N-Hydroxy-2-{5-[4-(N-hydroxyamidino)-phenyl]-furan-2-yl}-imidazo[1,2-a]pyridine-6-carboxamidine (5a); N-Hydroxy-2-{5-[4-(N-hydroxyamidino)-phenyl]-furan-2-yl}-8-methyl-imidazo[1,2-a]pyridine-6-carboxamidine (5b); N-Hydroxy-2-[4'-(N-hydroxyamidino)-biphenyl-4-yl]-imidazo[1,2-a]pyridine-6-carboxamidine (11a); N-Hydroxy-2-[4'-(N-hydroxyamidino)-biphenyl-3-yl]-imidazo[1,2-a]pyridine-6-carboxamidine (11b); N-Hydroxy-2-[4'-(N-hydroxyamidino)-biphenyl-3-yl]-8-methyl-imidazo[1,2-a]pyridine-6-carboxamidine (11c); 2,6-Bis[4-(N-hydroxyamidino-phenyl)]-imidazo[1,2-a]pyridine (17); and 2,6-Bis[4-(N-hydroxyamidino-phenyl)]-8-methyl-imidazo[1,2-a]pyridine (22).

In some embodiments, the method further comprises reacting the imidazo[1,2-a]pyridine bis-amidoxime formed in step (e) immediately hereinabove with an alkylating agent to form an imidazo[1,2-a]pyridine bis-O-alkylamidoxime of Formula (I). In some embodiments, the alkylating agent comprises a dialkyl sulfate. In some embodiments, the dialkyl sulfate comprises dimethyl sulfate. In some embodiments, the imidazo[1,2-a]pyridine bis-O-alkylamidoxime is selected from the group consisting of: N-Methoxy-2-{5-[4-(N-methoxyamidino)-phenyl]-furan-2-yl}-imidazo[1,2-a]pyridine-6-carboxamidine (6); and N-Methoxy-2-[4'-(N-methoxyamidino)-biphenyl-4-yl]-imidazo[1,2-a]pyridine-6-carboxamidine (12).

In some embodiments, the method further comprises:
(a) reacting the imidazo[1,2-a]pyridine bis-amidoxime with an acylating agent in a first protic solvent to form an acylated product;
(b) adding a second catalyst to the acylated product in a second protic solvent to form a third reaction mixture; and
(c) exposing the third reaction mixture to hydrogen under pressure for a period of time to form one of:
(i) a saturated imidazo[1,2-a]pyridine diamidine of Formula (I); and
(ii) an unsaturated imidazo[1,2-a]pyridine diamidine of Formula (I).

In some embodiments, the acylating agent comprises acetic anhydride. In some embodiments, the second catalyst comprises a palladium on carbon catalyst. In some embodiments, the first protic solvent comprises an acetic acid. In some embodiments, the second protic solvent is selected from the group consisting of an acetic acid and an alkyl alcohol. In some embodiments, the method comprises exposing the third reaction mixture to hydrogen under pressure for a period of time in a mixture of an alkyl alcohol and an alkyl ester to form an unsaturated imidazo[1,2-a]pyridine diamidine of Formula (I). In some embodiments, the alkyl ester comprises ethyl acetate.

In some embodiments, the saturated imidazo[1,2-a]pyridine diamidine formed in step (c)(i) immediately hereinabove is selected from the group consisting of: 2-[5-(4-Amidinophenyl)-furan-2-yl]-5,6,7,8-tetrahydro-imidazo[1,2-a]pyridine-6-carboxamidine (7); 2-(4'-Amidino-biphenyl-4-yl)-5,6,7,8-tetrahydro-imidazo[1,2-a]pyridine-6-carboxamidine (13a); 2-(4'-Amidinobiphenyl-3-yl)-5,6,7,8-tetrahydro-imidazo[1,2-a]pyridine-6-carboxamidine acetate salt (13b); and 2,6-Bis[4-Amidinophenyl)]-5,6,7,8-tetrahydro-imidazo[1,2-a]pyridine (18).

In some embodiments, the unsaturated imidazo[1,2-a]pyridine diamidine formed in step (c)(ii) immediately hereinabove is selected from the group consisting of: 2-[5-(4-Amidinophenyl)-furan-2-yl]-imidazo[1,2-a]pyridine-6-carboxamidine acetate salt (8a); 2-[5-(4-Amidinophenyl)-furan-2-yl]-8-methyl-imidazo[1,2-a]pyridine-6-carboxamidine acetate salt (8b); 2-(4'-Amidino-biphenyl-4-yl)-imidazo[1,2-a]pyridine-6-carboxamidine (14a); 2-(4'-Amidinobiphenyl-3-yl)-imidazo[1,2-a]pyridine-6-carboxamidine acetate salt (14b); 2-(4'-Amidinobiphenyl-3-yl)-8-methyl-imidazo[1,2-a]pyridine-6-carboxamidine acetate salt (14c); 2,6-Bis[4-amidinophenyl)]-imidazo[1,2-a]pyridine (19); and 2,6-Bis[4-amidinophenyl)]-8-methyl-imidazo[1,2-a]pyridine (23), or a pharmaceutically acceptable salt thereof.

V.A. General Process for the Synthesis of Diamidino Imidazo[1,2-a]pyridine and 5,6,7,8-tetrahydro-imidizao[1,2-a]pyridine Compounds of Formula (I) Comprising a Furanyl Linking Group In some embodiments, the method for preparing a diamidino imidazo[1,2-a]pyridine and 5,6,7,8-tetrahydro-imidizao[1,2-a]pyridine compound of Formula (I) comprising a furanyl linking group comprises:
(a) reacting 2-acetylfuran with a N-bromosuccinimide to form 1-(5-Bromo-furan-2-yl)-ethanone (1);
(b) adding bromine to 1-(5-Bromo-furan-2-yl)-ethanone (1) to form 2-Bromo-1-(5-bromo-furan-2-yl)-ethanone (2);
(c) refluxing a mixture of 2-Bromo-1-(5-bromo-furan-2-yl)-ethanone (2) and one of 6-Amino-nicotinonitrile or 6-Amino-5-methyl-nicotinitrile for a period of time to form one of 2-(5-Bromo-furan-2-yl)-imidazo[1,2-a]pyridine-6-carbonitrile (3a) or 2-(5-Bromo-furan-2-yl)-8-methyl-imidazo[1,2-a]pyridine-6-carbonitrile (3b);

(d) mixing one of 2-(5-Bromo-furan-2-yl)-imidazo[1,2-a]pyridine-6-carbonitrile (3a) or 2-(5-Bromo-furan-2-yl)-8-methyl-imidazo[1,2-a]pyridine-6-carbonitrile (3b) with tetrakis(triphenylphosphine)palladium to form a first reaction mixture; adding a solution of $Na_2CO_3$ to the first reaction mixture to form a second reaction mixture; and then adding 4-Cyanophenyl boronic acid to the second reaction mixture to form one of 2-[5-(4-Cyanophenyl)-furan-2-yl]-imidazo[1,2-a]pyridine-6-carbonitrile (4a) or 2-[5-(4-Cyanophenyl)-furan-2-yl]-8-methyl-imidazo[1,2-a]pyridine-6-carbonitrile (4b);

(e) adding potassium t-butoxide to a mixture of hydroxylamine hydrochloride in anhydrous DMSO to form a third reaction mixture and then adding the third reaction mixture to one of 2-[5-(4-Cyanophenyl)-furan-2-yl]-imidazo[1,2-a]pyridine-6-carbonitrile (4a) or 2-[5-(4-Cyanophenyl)-furan-2-yl]-8-methyl-imidazo[1,2-a]pyridine-6-carbonitrile (4b) to form one of N-Hydroxy-2-{5-[4-(N-hydroxyamidino)-phenyl]-furan-2-yl}-imidazo[1,2-a]pyridine-6-carboxamidine (5a) or N-Hydroxy-2-{5-[4-(N-hydroxyamidino)-phenyl]-furan-2-yl}-8-methyl-imidazo[1,2-a]pyridine-6-carboxamidine (5b);

(f) reacting one of N-Hydroxy-2-{5-[4-(N-hydroxyamidino)-phenyl]-furan-2-yl}-imidazo[1,2-a]pyridine-6-carboxamidine (5a) or N-Hydroxy-2-{5-[4-(N-hydroxyamidino)-phenyl]-furan-2-yl}-8-methyl-imidazo[1,2-a]pyridine-6-carboxamidine (5b) with one of:

(i) dimethyl sulfate in dioxane/NaOH to form N-Methoxy-2-{5-[4-(N-methoxyamidino)phenyl]-furan-2-yl}-imidazo[1,2-a]pyridine-6-carboxamidine (6);

(ii) acetic anhydride in glacial acetic acid to form an acylated product; adding 10% palladium on carbon to the solution of the acylated product in glacial acetic acid; and then exposing the solution to hydrogen under pressure to form 2-[5-(4-Amidino-phenyl)-furan-2-yl]-5,6,7,8-tetrahydro-imidazo[1,2-a]pyridine-6-carboxamidine (7); or (iii) acetic anhydride in glacial acetic acid to form an acylated product; adding 10% palladium on carbon in a mixture of ethanol/EtOAc to the acylated product; and then exposing the mixture to hydrogen under pressure to form one of 2-[5-(4-Amidino-phenyl)-furan-2-yl]-imidazo[1,2-a]pyridine-6-carboxamidine (8a) or 2-[5-(4-Amidino-phenyl)-furan-2-yl]-8-methyl-imidazo[1,2-a]pyridine-6-carboxamidine (8b).

V.B. General Process for the Synthesis of Diamidino Imidazo[1,2-a]pyridine and 5,6,7,8-tetrahydro-imidizao[2-a]pyridine Compounds of Formula (I) Comprising a Phenylene Linking Group In some embodiments, the method for preparing a diamidino imidazo[1,2-a]pyridine and 5,6,7,8-tetrahydro-imidizao[1,2-a]pyridine compounds of Formula (I) comprising a phenylene linking group comprises:

(a) refluxing a mixture of one of a 3- or 4-Bromophenacyl bromide and one of 6-Amino-nicotinonitrile or 6-Amino-5-methyl-nicotinonitrile for a period of time to form one of 2-(4-Bromophenyl)-imidazo[1,2-a]pyridine-6-carbonitrile (9a), 2-(3-Bromophenyl)-imidazo[1,2-a]pyridine-6-carbonitrile (9b), or 2-(3-Bromophenyl)-8-methyl-imidazo[1,2-a]pyridine-6-carbonitrile (9c).

(b) mixing one of 2-(4-Bromophenyl)-imidazo[1,2-a]pyridine-6-carbonitrile (9a), 2-(3-Bromophenyl)-imidazo[1,2-a]pyridine-6-carbonitrile (9b), or 2-(3-Bromophenyl)-8-methyl-imidazo[1,2-a]pyridine-6-carbonitrile (9c) with tetrakis(triphenylphosphine)palladium to form a first reaction mixture; adding a solution of $Na_2CO_3$ to the first reaction mixture to form a second reaction mixture; and then adding a solution of 4-Cyanophenyl boronic acid to the second reaction mixture to form one of 2-(4'-Cyano-biphenyl-4-yl)-imidazo[1,2-a]pyridine-6-carbonitrile (10a), 2-(4'-Cyano-biphenyl-3-yl)-imidazo[1,2-a]pyridine-6-carbonitrile (10b), or 2-(4'-Cyano-biphenyl-3-yl)-8-methyl-imidazo[1,2-a]pyridine-6-carbonitrile (10c);

(c) adding potassium t-butoxide to a mixture of hydroxylamine hydrochloride in anhydrous DMSO to form a third reaction mixture; adding the third reaction mixture to one of 2-(4'-Cyano-biphenyl-4-yl)-imidazo[1,2-a]pyridine-6-carbonitrile (10a), 2-(4'-Cyano-biphenyl-3-yl)-imidazo[1,2-a]pyridine-6-carbonitrile (10b), or 2-(4'-Cyano-biphenyl-3-yl)-8-methyl-imidazo[1,2-a]pyridine-6-carbonitrile (10c) to form N-Hydroxy-2-[4'-(N-hydroxyamidino)-biphenyl-4-yl]-imidazo[1,2-a]pyridine-6-carboxamidine (11a), N-Hydroxy-2-[4'-(N-hydroxyamidino)-biphenyl-3-yl]-imidazo[1,2-a]pyridine-6-carboxamidine (11b), or N-Hydroxy-2-[4'-(N-hydroxyamidino)-biphenyl-3-yl]-8-methyl-imidazo[1,2-a]pyridine-6-carboxamidine (11c);

(d) reacting one of N-Hydroxy-2-[4'-(N-hydroxyamidino)-biphenyl-4-yl]-imidazo[1,2-a]pyridine-6-carboxamidine (11a), N-Hydroxy-2-[4'-(N-hydroxyamidino)-biphenyl-3-yl]-imidazo[1,2-a]pyridine-6-carboxamidine (11b), or N-Hydroxy-2-[4'-(N-hydroxyamidino)-biphenyl-3-yl]-8-methyl-imidazo[1,2-a]pyridine-6-carboxamidine (11c); with one of:

(i) dimethyl sulfate in dioxane/NaOH to form N-Methoxy-2-[4'-(N-methoxyamidino)-biphenyl-4-yl]-imidazo[1,2-a]pyridine-6-carboxamidine (12);

(ii) acetic anhydride in glacial acetic acid to form an acylated product; adding 10% palladium on carbon to the solution of the acylated product in glacial acetic acid; and then exposing the solution to hydrogen under pressure for a period of time at room temperature to form one of 2-(4'-Amidino-biphenyl-4-yl)-5,6,7,8-tetrahydro-imidazo[1,2-a]pyridine-6-carboxamidine (13a) or 2-(4'-Amidino-biphenyl-3-yl)-5,6,7,8-tetrahydro-imidazo[1,2-a]pyridine-6-carboxamidine (13b) or (iii) acetic anhydride in glacial acetic acid to form an acylated product; adding 10% palladium on carbon in a mixture of ethanol/EtOAc; exposing the mixture to hydrogen at an elevated pressure for a period of time to form one of 2-(4'-Amidino-biphenyl-4-yl)-imidazo[1,2-a]pyridine-6-carboxamidine (14a), 2-(4'-Amidino-biphenyl-3-yl)-imidazo[1,2-a]pyridine-6-carboxamidine (14b), or 2-(4'-Amidino-biphenyl-3-yl)-8-methyl-imidazo[1,2-a]pyridine-6-carboxamidine (14c).

V.C. General Process for the Synthesis of Diamidino Imidazo[1,2-a]pyridine and 5,6,7,8-tetrahydro-imidizao[1,2-a]

pyridine Compounds of Formula (I) Comprising Imidazo[1,2-a]pyridine or 5,6,7,8-tetrahydro-imidazo[1,2-a]pyridine as the Linking or Spacing Group In some embodiments, the method for preparing a diamidino imidazo[1,2-a]pyridine and 5,6,7,8-tetrahydro-imidizao [1,2-a]pyridine compound of Formula (I) comprising one of imidazo[1,2-a]pyridine or 5,6,7,8-tetrahydro-imidazo[1,2-a] pyridine as the linking or spacing group comprises:

(a) refluxing a mixture of 4-Cyanophenacyl bromide and one of 2-Amino-5-bromopyridine or 2-Amino-5-bromo-3-methylyridine for a period of time to form one of 4-(6-Bromo-imidazl[1,2-a]pyridine-2-yl)-benzonitrile (15) or 4-(6-Bromo-8-methyl-imidazo[1,2-a]pyridin-2-yl)-benzonitrile (20);

(b) mixing one of 4-(6-Bromo-imidazo[1,2-a]pyridine-2-yl)-benzonitrile (15) or 4-(6-Bromo-8-methyl-imidazo[1,2-a]pyridin-2-yl)-benzonitrile (20) with tetrakis (triphenylphosphine)palladium to form a first reaction mixture; adding a solution of $Na_2CO_3$ to the first reaction mixture to form a second reaction mixture; adding 4-Cyanophenyl boronic acid to the second reaction mixture to form one of 2,6-Bis(4-cyanophenyl)-imidazo[1,2-a]pyridine (16) or 2,6-Bis(4-cyanophenyl)-8-methyl-imidazo[1,2-a]pyridine (21);

(c) adding potassium t-butoxide to a mixture of hydroxylamine hydrochloride in anhydrous DMSO to form a third reaction mixture;

(d) adding the third reaction mixture to one of 2,6-Bis(4-cyanophenyl)-imidazo[1,2-a]pyridine (16) or 2,6-Bis(4-cyanophenyl)-8-methyl-imidazo[1,2-a]pyridine (21) to form one of 2,6-Bis[4-(N-hydroxyamidino-phenyl)]-imidazo[1,2-a]pyridine (17) or 2,6-Bis[4-(N-hydroxyamidino-phenyl)]-8-methyl-imidazo[1,2-a]pyridine (22);

(e) reacting one of 2,6-Bis[4-(N-hydroxyamidino-phenyl)]-imidazo[1,2-a]pyridine (17) or 2,6-Bis[4-(N-hydroxyamidino-phenyl)]-8-methyl-imidazo[1,2-a]pyridine (22) in one of:

(i) acetic anhydride in glacial acetic acid to form an acylated product; adding 10% palladium on carbon to the solution of the acylated product in glacial acetic acid; and then exposing the solution to hydrogen under pressure for a period of time at room temperature to form 2,6-Bis[4-amidinophenyl)]-5,6,7,8-tetrahydro-imidazo[1,2-a]pyridine (18); or (ii) acetic anhydride in glacial acetic acid to form an acylated product; adding 10% palladium on carbon in a mixture of ethanol/EtOAc; exposing the mixture to hydrogen at an elevated pressure for a period of time to form one of 2,6-Bis[amidinophenyl)]-imidazo[1,2-a]pyridine (19) or 2,6-Bis[4-amidinophenyl)]-8-methyl-imidazo[1,2-a]pyridine (23);

or a pharmaceutically acceptable salt thereof.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Methods and Materials for Examples 1-4

Melting points were recorded using a Thomas-Hoover (Uni-Melt) capillary melting point apparatus (Thomas Scientific, Swedesboro, N.J., United States of America) and are uncorrected. TLC analysis was carried out on silica gel 60 $F_{254}$ precoated aluminum sheets and detected under UV light. $^1H$ and $^{13}C$ NMR spectra were recorded employing a Varian GX400 or Varian Unity Plus 300 spectrometer (Varian, Inc., Palo Alto, Calif., United States of America), and chemical shifts (δ) are in ppm relative to TMS as internal standard. Mass spectra were recorded on a VG analytical 70-SE spectrometer. Elemental analyses were obtained from Atlantic Microlab Inc. (Norcross, Ga., United States of America) and are within ±0.4 of the theoretical values. The compounds reported as salts were frequently analyzed for fractional moles by water and/or ethanol of solvation. In each case proton NMR showed the presence of the indicated solvent(s). All chemicals and solvents were purchased from Aldrich Chemical Co. (St. Louis, Mo., United States of America), Fisher Scientific (Fairlawn, N.J., United States of America), Frontier Scientific (Logan, Utah, United States of America) or Lancaster Synthesis, Inc. (Windham, N.H., United States of America).

Example 1

Referring now to Scheme 2, the acetate salt of 2-[5-(4-Amidinophenyl)-furan-2-yl]-5,6,7,8-tetrahydro-imidazo[1,2-a]pyridine-6-carboxamidine (7) was synthesized from 2-[5-(4-Cyanophenyl)-furan-2-yl]-imidazo[1,2-a]pyridine-6-carbonitrile (4a), through the bis-O-acetoxyamidoxime followed by hydrogenation in glacial acetic acid. Compound 4a was obtained in four steps starting with two successive brominations of 2-acetylfuran first with N-bromosuccinimide, and second with bromine to form 2-Bromo-1-(5-bromofuran-2-yl)-ethanone (2) in a moderate yield. A condensation reaction between 6-Amino-nicotinonitrile and compound 2 gave 2-(5-Bromofuran-2-yl)-imidazo[1,2-a]pyridine-6-carbonitrile (3a). A subsequent Suzuki coupling of 3a with 4-Cyanophenyl boronic acid furnished 4a in good yield. Interestingly, 2-[5-(4-Amidinophenyl)-furan-2-y]-imidazo[1,2-a] pyridine-6-carbox-amidine acetate salt (8a) was obtained from 4a, through the bis-O-acetoxyamidoxime followed by hydrogenation in a mixture of ethanol/ethylacetate. Thus, by choice of hydrogenation solvent the saturated or unsaturated imidazo[1,2-a]pyridine can be obtained.

Diamidine 8b was prepared starting from 4b which was obtained by an analogous procedure to that described for 4a employing 2-(5-Bromofuran-2-yl)-8-methyl-imidazo[1,2-a] pyridine-6-carbonitrile (3b) instead of 3a. In this case, however, the tetrahydro-analogue of the diamidine 8b was not obtained by using acetic acid as the hydrogenation solvent as described for the diamidine 7. This result could be due to the steric effect of the methyl group. The potential prodrug, N-Methoxy-2-{5-[4-(N-methoxyamidino)-phenyl]-furan-2-yl}-imidazo[1,2-a]pyridine-6-carboxamidine (6), was prepared via methylation of the respective diamidoxime 5a with dimethyl sulfate in aqueous sodium hydroxide solution at 0° C. in a reasonable yield (see Scheme 2).

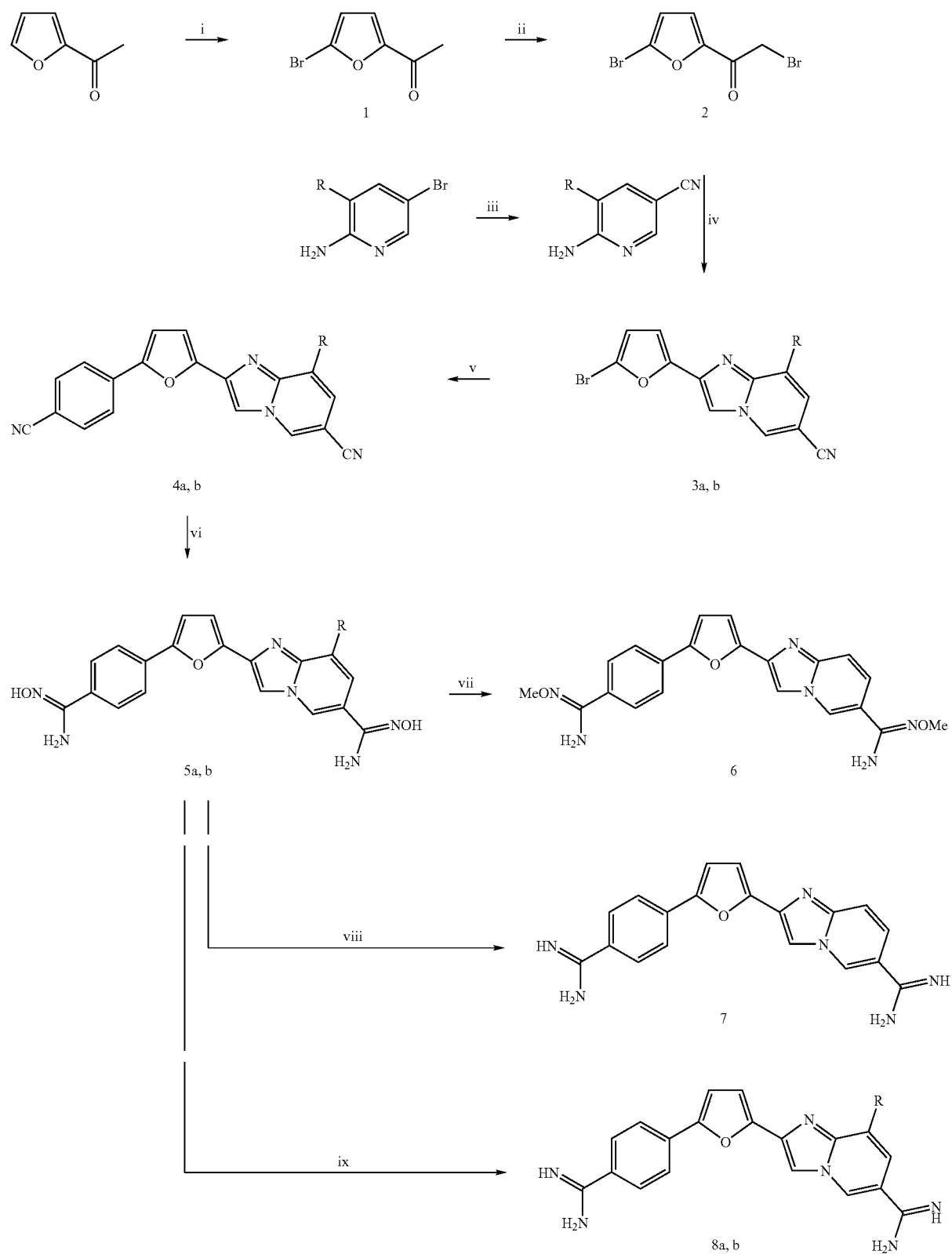
Scheme 2

3, 4, 5, 8: a, R = H; b, R = Me

Reagents and conditions:
i NBS, DMF;
ii Br$_2$;
iii Cu(I)CN, DMF;
iv EtOH, reflux;
v 4-Cyanophenyl boronic acid, Pd(PPh$_3$)$_4$;
vi NH$_2$OH·HCl/K—O-t-Bu, DMSO;
vii (Me)$_2$SO$_4$;
viii a) Ac$_2$O/AcOH, b) H$_2$/Pd——C, AcOH;
ix a) Ac$_2$O/AcOH, b) H$_2$/Pd——C, EtOH

Example 2

Diamidines comprising 1,4-phenyl and 1,3-phenyl rings instead of the furan ring as the spacer, or linking group, also were prepared. Referring now to Scheme 3, the synthesis of 2-(4'-Amidinobiphenyl-4-yl)-5,6,7,8-tetrahydro-imidazo[1,2-a]pyridine-6-carboxamidine acetate salt (13a) employed an analogous synthetic approach to that used for 7 starting from the corresponding bis-O-acetoxyamidoxime. The required dinitrile 10a was obtained using a similar synthetic approach to that employed for 4a by starting with 4-Bromophenacyl bromide instead of 2 in the preparation of 2-(4-Bromophenyl)-imidazo[1,2-a]pyridine-6-carbonitrile (9a). On the other hand, the synthesis of 2-(4'-Amidinobiphenyl-4-yl)-imidazo[1,2-a]pyridine-6-carboxamidine (14a) employed the analogous synthetic approach as used for 8a. N-Methoxy-2-[4'-(N-methoxyamidino)-biphenyl-4-yl]-imidazo[1,2-a]pyridine-6-carboxamidine (12), a potential prodrug of diamidine 14a, was prepared in a similar way to that of 6 starting with the respective diamidoxime 11a. The hydrochloride salts of all the amidoximes, 5a, 6, 11a and 12 were made by passing hydrogen chloride gas into an ethanolic solution of the free bases.

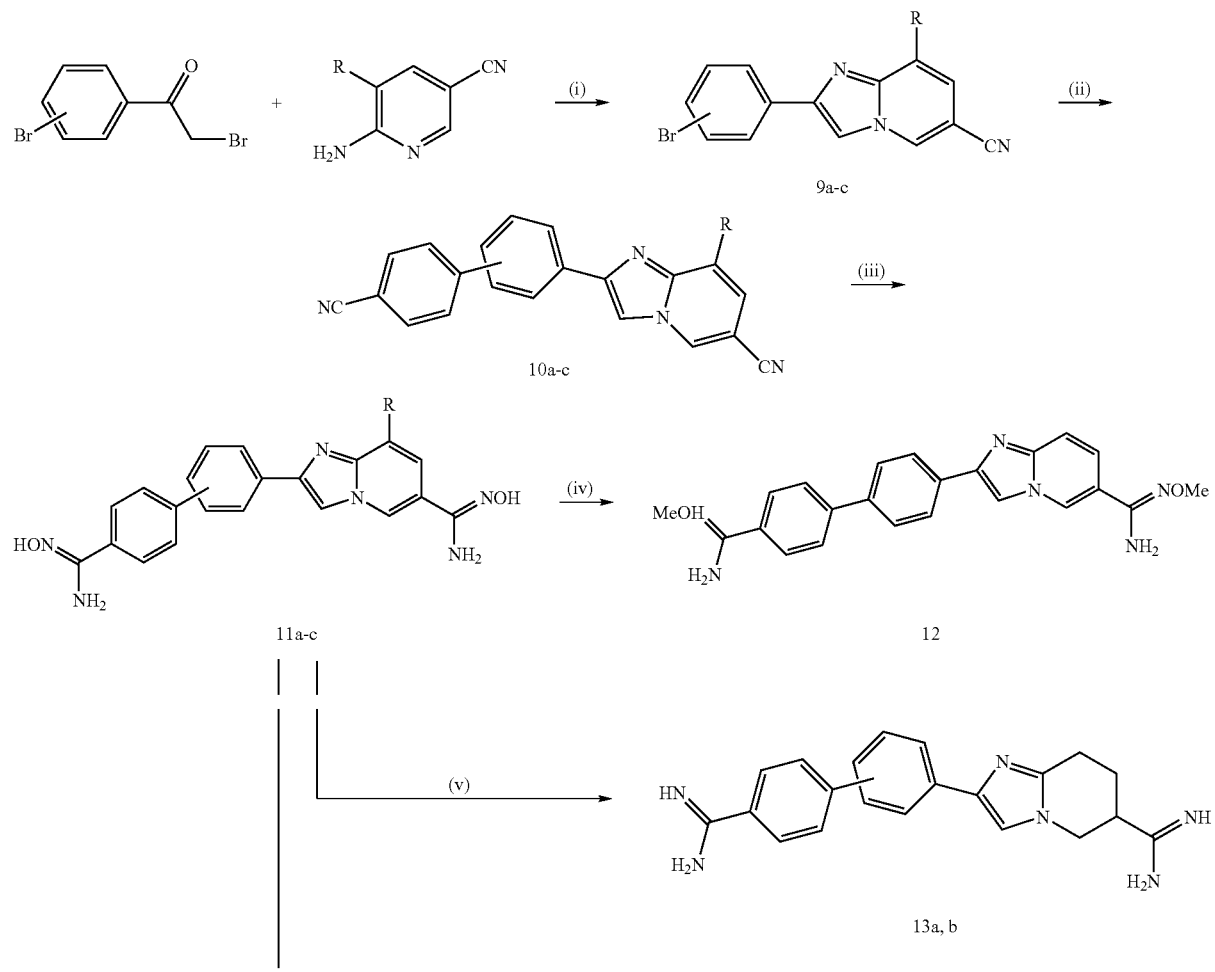

Scheme 3

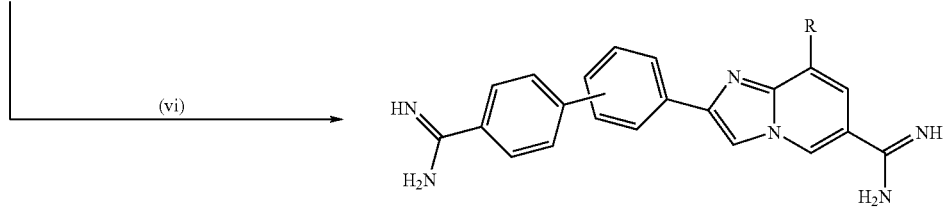

9a, 10a, 11a, 13a, 14a; R = H; para connection
9b, 10b, 11b, 13b, 14b; R = H; meta connection
9c, 10c, 11c, 14c; R = Me; meta connection Reagents and conditions:
(i) EtOH, reflux;
(ii) 4-Cyanophenyl boronic acid, Pd(PPh₃)₄;
(iii) NH₂OH•HCl/K—O-t-Bu, DMSO;
(iv) (Me)₂SO₄: (v) a) Ac₂O/AcOH, b) H₂/Pd—C, AcOH;
(vi) a) Ac₂O/AcOH, b) H₂/Pd—C, EtOH

Example 3

Referring now to Scheme 4, a multi-step procedure similar to that described in Schemes 2 and 3 is provided for the preparation of 2,6-Bis(4-amidinophenyl)-5,6,7,8-tetrahydro-imidazo[1,2-a]pyridine acetate salt (18) and 2,6-Bis(4-amidinophenyl)-imidazo[1,2-a]pyridine acetate salt (19) employing imidazo[1,2-a]pyridine and its tetrahydro-form as new spacers, or linking groups.

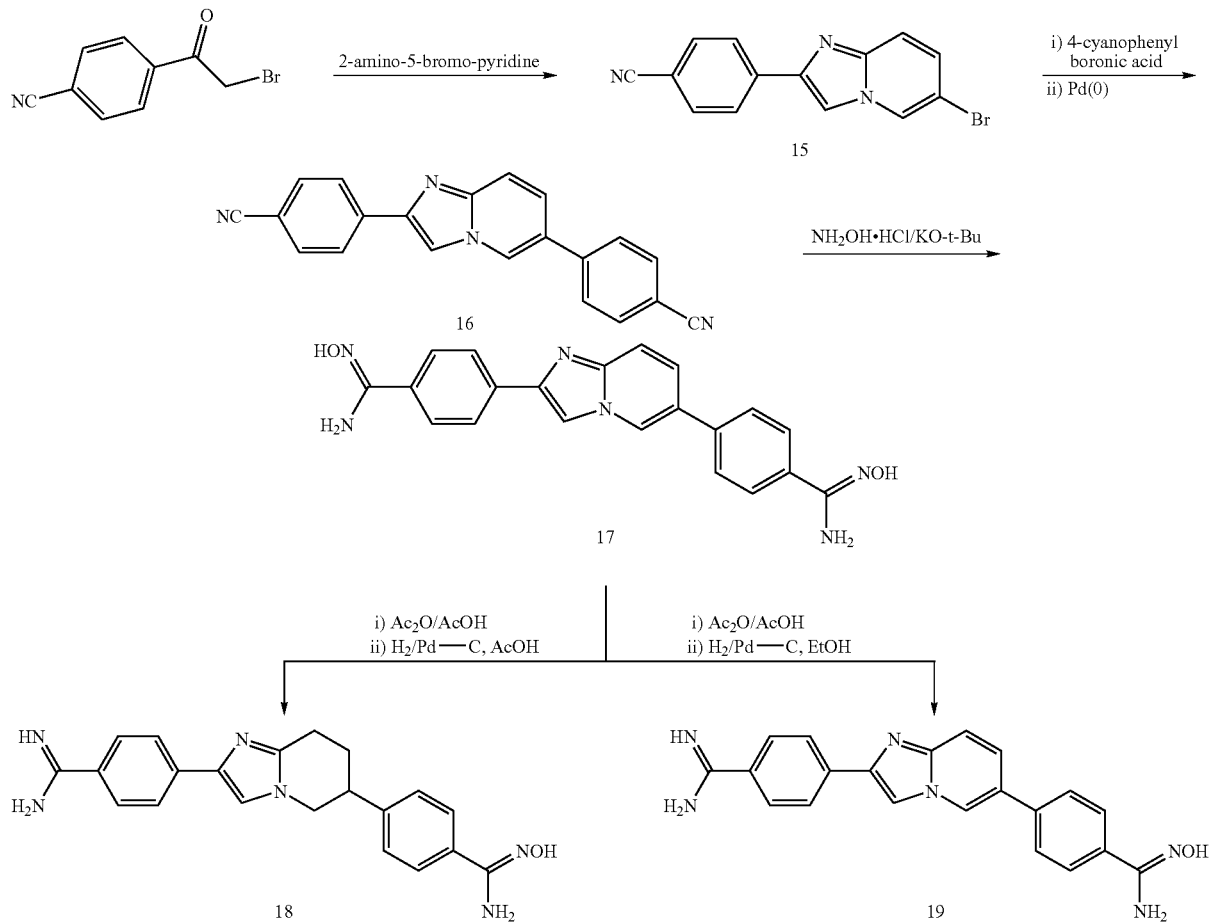

Example 4

Referring now to Scheme 5, a multi-step procedure similar to that described in Scheme 4 is provided to describe the preparation of 2,6-Bis[4-(N-hydroxyamidino-phenyl)]-8-methyl-imidazo[1,2-a]pyridine (22) and 2,6-Bis[4-amidinophenyl)]-8-methyl-imidazo[1,2-a]pyridine acetate salt (23).

12 mL dioxane/ether (1:2) with cooling at 0-5° C. and stirring was portionwise added bromine (0.52 mL, 10 mmol) over 1 h. The reaction mixture was further stirred with cooling. After TLC indicated complete bromination, the reaction mixture was diluted with ether (50 mL) and water (100 mL). The ethereal layer was separated, washed with 1 M aqueous sodium bicarbonate solution, and dried over $Na_2SO_4$. The ether extract was distilled to afford 2 in 65% yield, mp 96-97°

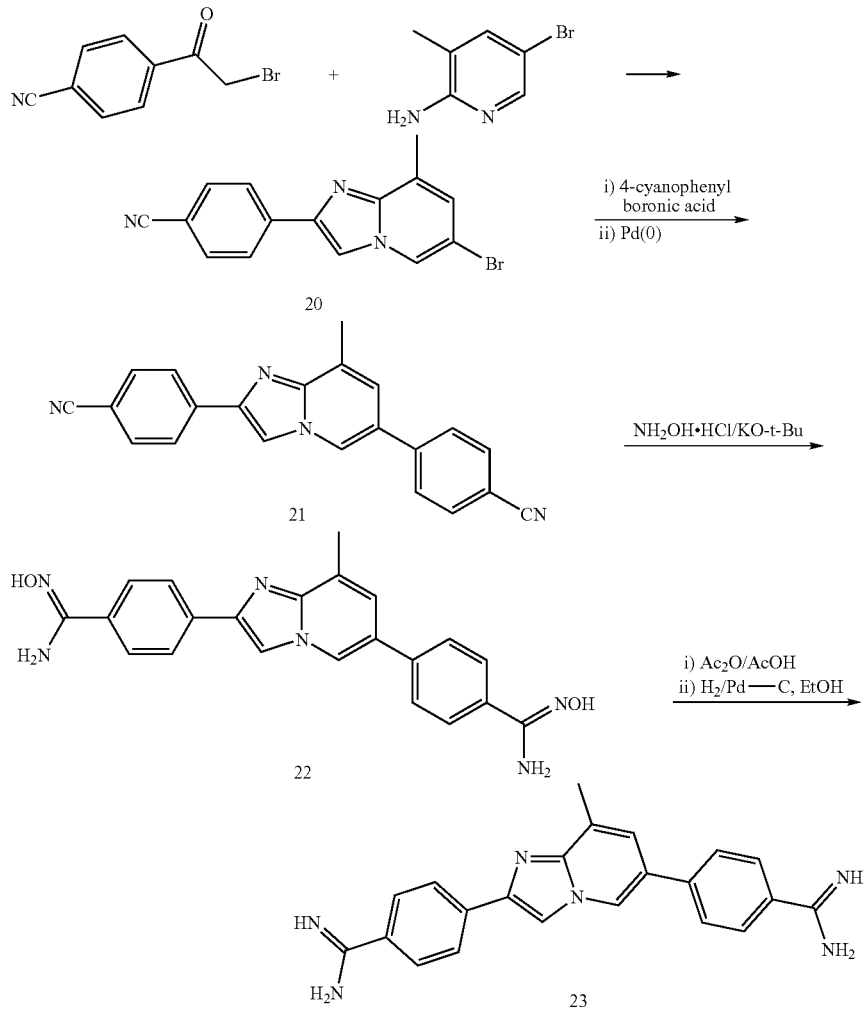

Synthetic Methods and Supporting Analytical Data 1-(5-Bromofuran-2-yl)-ethanone (1). To a solution of 2-acetylfuran (20 mmol) in DMF (20 mL) was added portionwise N-bromosuccinimide (22 mmol) with stirring. The reaction mixture was stirred overnight, then poured onto cold water. The product was extracted with ether (200 mL, 3× times). Yield 61%, mp 92-93° C. (hexanes/ether, Lit. mp 94-95° C.; see Gilman H., et al., *J. Am. Chem. Soc.*, 53, 4192-4196 (1931). $^1$H NMR (CDCl$_3$); δ 2.45 (s, 3H), 6.49 (d, J=3.9 Hz, 1H), 7.12 (d, J=3.6 Hz, 1H). $^{13}$C NMR; δ 8185.4, 154.4, 128.2, 118.9, 114.3, 25.7.

2-Bromo-1-(5-bromofuran-2-yl)-ethanone (2). To a solution of 1-(5-Bromofuran-2-yl)-ethanone (1.88 g, 10 mmol) in C. (hexanes/ether, Lit. mp 98.5-99.5° C.; see Brown E., *Iowa State Coll. J. Sci.*, 11, 221-225 (1937)). $^1$H NMR (CDCl$_3$); δ 4.24 (s, 2H), 6.55 (d, J=3.6 Hz, 1H), 7.27 (d, J=3.6 Hz, 1H).

$^{13}$C NMR; δ 179.0, 151.9, 129.4, 121.1, 115.0, 29.5.

2-(5-Bromofuran-2-yl)-imidazo[1,2-a]pyridine-6-carbonitrile (3a). A mixture of 6-Amino-nicotinonitrile (1.19 g, 10 mmol) and 2-Bromo-1-(5-bromofuran-2-yl)-ethanone (2.66 g, 10 mmol) in ethanol (50 mL) was refluxed for 24 h. The precipitate was filtered and neutralized with aqueous NaHCO$_3$ solution. The precipitate was filtered and dried to furnish 3a in 74% yield, mp 212-214° C. (EtOH). $^1$H NMR (DMSO-d$_6$); δ 6.75 (d, J=3.6 Hz, 1H), 6.98 (d, J=3.6 Hz, 1H), 7.54 (d, J=8.4 Hz, 1H), 7.71 (d, J=8.4 Hz, 1H), 8.29 (s, 1H), 9.30 (s, 1H). $^{13}$C NMR; δ 150.5, 144.2, 137.3, 134.3, 125.4, 121.9, 117.2, 116.9, 113.9, 110.4, 109.8, 97.2. MS (m/z, rel.int.); 288 (M+, 100), 161 (8). Anal. Calcd. for 3a ($C_{12}H_6BrN_3O$): C % 50.03, H % 2.10. Found: C % 49.97, H % 2.17.

2-[5-(4-Cyanophenyl)-furan-2-yl]-imidazo[1,2-a]pyridine-6-carbonitrile (4a). To a stirred solution of 3a (10 mmol), and tetrakis(triphenylphosphine) palladium (350 mg) in toluene (20 mL) under a nitrogen atmosphere was added 10 mL of a 2 M aqueous solution of $Na_2CO_3$ followed by 4-Cyanophenyl boronic acid (12 mmol) in 10 mL of methanol. The vigorously stirred mixture was warmed to 80° C. for 24 h, then cooled, and the precipitate was filtered. The precipitate was partitioned between methylene chloride (500 mL) and 2 M aqueous $Na_2CO_3$ (50 mL) containing 6 mL of concentrated ammonia. The organic layer was dried ($Na_2SO_4$), and then concentrated to dryness under reduced pressure to afford 4a. Yield 82%, mp 298-300° C. (DMF). $^1$H NMR (DMSO-$d_6$); δ 7.11 (d, J=3.6 Hz, 1H), 7.37 (d, J=3.6 Hz, 1H), 7.53 (d, J=9.6 Hz, 1H), 7.72 (d, J=9.6 Hz, 1H), 7.90 (d, J=8.4 Hz, 2H), 7.98 (d, J=8.4 Hz, 2H), 8.45 (s, 1H), 9.32 (s, 1H). $^{13}$C NMR; δ 152.0, 150.4, 145.1, 138.6, 135.0, 134.4, 133.6, 126.1, 124.6, 119.5, 118.0, 117.6, 112.2, 111.3, 110.2, 98.1. MS (m/z, rel.int.); 310 (M+, 100), 281 (10), 208 (5), 180 (10). High resolution mass calcd. for $C_{19}H_{10}N_4O$: 310.08546. Observed: 310.07852. Anal. Calcd. for 4a ($C_{19}H_{10}N_4O$): C % 73.54, H % 3.25, N % 18.06. Found: C % 73.28, H % 3.26, N % 17.75.

N-Hydroxy-2-{(5-[4-(N-hydroxyamidino)-phenyl]-furan-2-yl}-imidazo[1,2-a]pyridine-6-carboxamidine hydrochloride salt (5a). A mixture of hydroxylamine hydrochloride (5.2 g, 75 mmol, 10 eq.) in anhydrous DMSO (40 mL) was cooled to 5° C. under nitrogen and potassium t-butoxide (8.4 g, 75 mmol, 10 eq.) was added in portions. The mixture was stirred for 30 min. This mixture was added to the bis cyano derivative 4a (7.5 mmol, 1 eq.). The reaction mixture was stirred overnight at room temperature. The reaction mixture was then poured slowly onto ice-water (200 mL). The precipitate was filtered and washed with water to afford 5a (free base) in 96% yield, mp 207-210° C. $^1$H NMR (DMSO-$d_6$); δ 5.85 (s, 2H), 5.97 (s, 2H), 6.97 (d, J=3.6 Hz, 1H), 7.14 (d, J=3.6 Hz, 1H), 7.54-7.56 (m, 2H), 7.76 (d, J=8.4 Hz, 2H), 7.82 (d, J=8.4 Hz, 2H), 8.35 (s, 1H), 8.80 (s, 1H), 9.70 (s, 1H), 9.83 (s, 1H). $^{13}$C NMR; δ 152.1, 150.3, 149.2, 148.5, 144.7, 136.9, 132.1, 130.2, 125.8, 124.1, 123.7, 123.0, 119.2, 115.6, 109.5, 109.1, 108.5. (5a, hydrochloride salt), mp 289-291° C. Anal. Calcd. for 5a ($C_{19}H_{16}N_6O_3 \cdot 3.0HCl \cdot 1.9H_2O$): C % 43.88, H % 4.41, N % 16.16, Cl % 20.45. Found: C % 44.25, H % 4.18, N % 15.89, Cl % 20.10.

N-Methoxy-2{5-[4-(N-methoxyamidino)-phenyl]-furan-2-yl}-imidazo[1,2-a]pyridine-6-carboxamidine hydrochloride salt (6). To a solution of 5a (3 mmol) in dioxane (5 mL) and 2 N NaOH (24 mL) at 0-5° C., was slowly added dimethyl sulfate (9 mmol) in dioxane (5 mL). The reaction mixture was further stirred for 2 h and then extracted with ethylacetate (200 mL, 3 times). The solvent was evaporated and the residue was purified ($SiO_2$, hexanes/EtOAc, 2:8) to give 6 (free base) in 43% yield, mp 126-127° C. $^1$H NMR (DMSO-$d_6$); δ 3.77 (s, 6H), 6.12 (s, 2H), 6.23 (s, 2H), 6.99 (d, J=3.6 Hz, 1H), 7.18 (d, J=3.6 Hz, 1H), 7.55 (s, 2H), 7.76 (d, J=8.4 Hz, 2H), 7.82 (d, J=8.4 Hz, 2H), 8.38 (s, 1H), 8.84 (s, 1H). $^{13}$C NMR; δ 152.1, 150.6, 149.2, 148.9, 144.8, 137.0, 131.3, 130.7, 126.2, 124.7, 123.8, 123.0, 118.4, 115.7, 109.6, 109.2, 108.7, 60.7, 60.6. MS (m/z, rel.int.); 404 (M+, 100), 373 (10), 357 (50), 326 (20), 310 (25). High resolution mass calcd. for $C_{21}H_{20}N_6O_3$: 404.15969. Observed: 404.15957. (6, hydrochloride salt), mp 208-209° C. Anal. Calcd. for 6 ($C_{21}H_{20}N_6O_3 \cdot 3.0HCl \cdot 1.5H_2O$): C % 46.63, H % 4.85, N % 15.53. Found: C % 46.64, H % 5.09, N % 15.17.

2-[5-(4-Amidinophenyl)-furan-2-yl]-5,6,7,8-tetrahydro-imidazo[1,2-a]pyridine-6-carboxamidine acetate salt (7). To a solution of 5a (1 mmol) in glacial acetic acid (10 mL) was slowly added acetic anhydride (0.35 mL). After stirring overnight, TLC indicated complete acylation of the starting material, and then the solvent was evaporated under reduced pressure. To the acylated product in glacial acetic acid (20 mL) was added 10% palladium on carbon (80 mg), then the mixture was placed in a Parr hydrogenation apparatus at 50 psi for 6 h at room temperature. The reaction mixture was filtered through hyflo and the filter pad washed with water. The filtrate was evaporated under reduced pressure and the precipitate was collected and washed with ether to give 7 in 86% yield, mp 195-197° C. $^1$H NMR ($D_2O$/DMSO-$d_6$); δ 1.80-2.10 (br s, 2.8×$CH_3$+3H), 2.80 (br s, 1H), 3.07 (br s, 1H), 4.10 (br s, 1H), 4.37 (br s, 1H), 6.64 (d, J=3.6 Hz, 1H), 7.22 (d, J=3.6 Hz, 1H), 7.57 (s, 1H), 7.81-7.90 (m, 4H). MS (m/z, rel.int.); 348 (M+, 5), 314 (100), 300 (5), 261 (8). Anal. Calcd. for 7 ($C_{19}H_{20}N_6O \cdot 2.8AcOH \cdot 2.0H_2O$): C % 53.46; H % 6.42, N % 15.20. Found: C % 53.23, H % 6.19, N % 15.40.

2-[5-(4-Amidinophenyl)-furan-2-yl]-imidazo[1,2-a]pyridine-6-carboxamidine acetate salt (8a). To a solution of 5a (1 mmol) in glacial acetic acid (10 mL) was slowly added acetic anhydride (0.35 mL). After stirring overnight, TLC indicated complete acylation of the starting material, and then the solvent was evaporated under reduced pressure. To the acylated product in a mixture of ethanol/EtOAc (50 mL, 1:1) was added 10% palladium on carbon (80 mg), then the mixture was placed in a Parr hydrogenation apparatus at 50 psi for 4 h at room temperature. The reaction mixture was filtered through hyflo and the filter pad washed with water. The filtrate was evaporated under reduced pressure and the precipitate was collected and washed with ether to give 8a in 71% yield, mp 257-259° C. $^1$H NMR ($D_2O$/DMSO-$d_6$); δ 1.76 (s, 2.7× $CH_3$), 7.09 (d, J=3.6 Hz, 1H), 7.36 (d, J=3.6 Hz, 1H), 7.59 (d, J=9.6 Hz, 1H), 7.71 (d, J=9.6 Hz, 1H), 7.89 (d, J=8.4 Hz, 2H), 8.00 (d, J=8.4 Hz, 2H), 8.52 (s, 1H), 9.13 (s, 1H). MS (m/z, rel.int.); 344 (M+, 5), 327 (20), 310 (100), 290 (55). Anal. Calcd. for 8a ($C_{19}H_{16}N_6O \cdot 2.7AcOH \cdot 2.0H_2O$): C % 54.02, H % 5.72, N % 15.49. Found: C % 54.06, H % 5.45, N % 15.81.

6-Amino-5-methylnicotinonitrile. A mixture of 2-Amino-5-bromo-3-methylpyridine (15.49 g, 82.8 mmol) and Cu(I) CN (9.27 g, 103.5 mmol) in DMF (160 mL) was heated at 150° C. for 24 h. The reaction mixture was poured onto water and the solid which formed was extracted by using ethylacetate (600 mL, 3 times) from aq. $NH_4OH$. The solvent was evaporated and the precipitate purified by chromatography ($SiO_2$, hexanes/EtOAc 4:6). Yield 70%, mp 198-200° C., (Lit. mp 203-205° C.; see Dunn A. D. and Norrie R. *J. Prakt. Chem./Chem.-Ztg*, 338 (7), 663-666 (1996). Lit. melting point not reported via palladium-catalyzed cyanation; see Maligres, P. et al., *Tetrahedron Lett.*, 40, 8193-8195 (1999).

2-(5-Bromofuran-2-yl)-8-methyl-imidazo[1,2-a]pyridine-6-carbonitrile (3b). The same procedure described for 3a was used employing 6-Amino-5-methylnicotinonitrile instead of 6-Amino-nicotinonitrile. Yield 72%, mp 204.5-205° C. $^1$H NMR (DMSO-$d_6$); δ 2.52 (s, 3H), 6.74 (d, J=3.6 Hz, 1H), 6.98 (d, J=3.6 Hz, 1H), 7.36 (s, 1H), 8.26 (s, 1H), 9.16 (s, 1H). $^{13}$C NMR; δ 150.6, 144.8, 136.7, 131.9, 127.4, 123.3, 121.6, 117.0, 113.8, 110.4, 110.1, 97.1, 16.3. Anal. Calcd. for 3b ($C_{13}H_8BrN_3O$): C % 51.68, H % 2.67. Found: C % 52.00, H % 2.73.

2-[5-(4-Cyanophenyl)-furan-2-yl]-8-methyl-imidazo[1,2-a]pyridine-6-carbonitrile (4b). The same procedure described for 4a was used starting with 3b. Yield 77%, mp 276-277° C.

¹H NMR (DMSO-d₆); δ 2.54 (s, 3H), 7.12 (d, J=3.6 Hz, 1H), 7.38 (s, 1H), 7.39 (d, J=3.6 Hz, 1H), 7.91 (d, J=8.4 Hz, 2H), 7.99 (d, J=8.4 Hz, 2H), 8.45 (s, 1H), 9.19 (s, 1H). ¹³C NMR; δ 151.1, 149.7, 144.9, 137.2, 133.6, 132.8, 132.0, 127.4, 123.8, 123.3, 118.8, 117.0, 111.4, 111.0, 110.3, 109.3, 97.1, 16.3. MS (m/z, rel.int.); 324 (M⁺, 100), 295 (7), 222 (8), 194 (15), 162 (15). High resolution mass calcd. for $C_{20}H_{12}N_4O$: 324.10111. Observed: 324.10070.

N-Hydroxy-2-{(5-[4-(N-hydroxyamidino)-phenyl]-furan-2-yl}-8-methyl-imidazo[1,2-a]pyridine-6-carboxamidine (5b). The same procedure described for 5a was used starting with 4b. Yield 92%, mp 255-258° C. ¹H NMR (DMSO-d₆); δ 2.54 (s, 3H), 5.91 (br s, 4H), 6.99 (d, J=3.6 Hz, 1H), 7.15 (d, J=3.6 Hz, 1H), 7.41 (s, 1H), 7.78 (d, J=8.7 Hz, 2H), 7.83 (d, J=8.7 Hz, 2H), 8.36 (s, 1H), 8.68 (s, 1H), 9.73 (s, 1H), 9.79 (s, 1H). ¹³C NMR; δ 152.0, 150.4, 149.4, 148.7, 145.2, 136.4, 132.0, 130.3, 125.8, 125.1, 123.0, 121.9, 119.1, 110.1, 108.9, 108.4, 16.7. Anal. Calcd. for 5b ($C_{20}H_{18}N_6O_3$·0.5H₂O): C % 60.12, H % 4.77. Found: C % 60.18, H % 5.03.

2-[5-(4-Amidinophenyl)-furan-2-yl]-8-methyl-imidazo[1,2-a]pyridine-6-carboxamidine acetate salt (8b). The same procedure described for 8a was used starting with 5b. Yield 68%, mp 229-231° C. ¹H NMR (D₂O/DMSO-d₆); δ 1.84 (s, 3×CH₃), 2.58 (s, 3H), 7.02 (d, J=3.6 Hz, 1H), 7.24 (d, J=3.6 Hz, 1H), 7.48 (s, 1H), 7.82-7.92 (m, 4H), 8.40 (s, 1H), 8.89 (s, 1H). Anal. Calcd. for 8b ($C_{20}H_{18}N_6O$·3.0AcOH·1.35H₂O): C % 55.47, H % 5.85. Found: C % 55.10, H % 5.91, N % 15.27.

2-(4-Bromophenyl)-imidazo[1,2-a]pyridine-6-carbonitrile (9a). The same procedure described for 3a was used employing 4-Bromophenacyl bromide instead of 2-Bromo-1-(5-bromofuran-2-yl)-ethanone (2). Yield 67%, mp 262-264° C. ¹H NMR (DMSO-d₆); δ 7.73 (d, J=8.4 Hz, 2H), 7.76 (d, J=9.6 Hz, 1H), 7.87 (d, J=9.6 Hz, 1H), 7.97 (d, J=8.4 Hz, 2H), 8.69 (s, 1H), 9.48 (s, 1H). Anal. Calcd. for 9a ($C_{14}H_8BrN_3$): C % 56.40, H % 2.70. Found: C % 56.31, H % 2.65.

2-(4'-Cyanobiphenyl-4-yl)-imidazo[1,2-a]pyridine-6-carbonitrile (10a). The same procedure described for 4a was used starting with 9a. Yield 78%, mp 276-278° C. ¹H NMR (DMSO-d₆); δ 7.51 (d, J=9.0 Hz, 1H), 7.76 (d, J=9.0 Hz, 1H), 7.87 (d, J=7.8 Hz, 2H), 7.92-7.98 (m, 4H), 8.14 (d, J=7.8 Hz, 2H), 8.58 (s, 1H), 9.33 (s, 1H). ¹³C NMR; δ 145.6, 144.2, 143.9, 137.9, 134.3, 133.2, 132.8, 127.5, 127.4, 126.6, 125.0, 118.8, 117.4, 117.1, 110.9, 110.0, 97.1. MS (m/z, rel.int.); 320 (M⁺, 100), 293 (5), 217 (8), 190 (8), 160 (10). High resolution mass calcd. for $C_{21}H_{12}N_4$: 320.10620. Observed: 320.10275. Anal. Calcd. for 10a ($C_{21}H_{12}N_4$·0.25H₂O): C % 77.64, H % 3.87, N % 17.24. Found: C % 77.56, H % 3.84, N % 16.91.

N-Hydroxy-2-[4'-(N-hydroxyamidino)-biphenyl-4-yl]-imidazo[1,2-a]pyridine-6-carboxamidine hydrochloride salt (11a). The same procedure described for 5a was used starting with 10a. Free base yield 97%, mp 300-302° C. ¹H NMR (DMSO-d₆); δ 5.86 (s, 2H), 5.94 (s, 2H), 7.55 (s, 2H), 7.72-7.80 (m, 6H), 8.07 (d, J=8.1 Hz, 2H), 8.47 (s, 1H), 8.80 (s, 1H), 9.69 (s, 1H), 9.83 (s, 1H). ¹³C NMR; δ 150.4, 148.5, 144.6, 144.4, 139.9, 138.7, 133.0, 132.3, 126.8, 126.16, 126.11, 125.9, 124.0, 123.2, 119.0, 115.8, 110.0. (11a, hydrochloride salt), mp 291-293° C. Anal. Calcd. for 11a ($C_{21}H_{18}N_6O_2$·3.0HCl·1.9H₂O·0.25EtOH): C % 47.68, H % 4.89, N % 15.51. Found: C % 47.89, H % 4.85, N % 15.25.

N-Methoxy-2-[4'-(N-methoxyamidino)-biphenyl-4-yl]-imidazo[1,2-a]pyridine-6-carboxamidine hydrochloride salt (12). The same procedure described for 6 was used starting with 11a. Free base yield 48%, mp 224-226° C. (SiO₂: hexanes/EtOAc; 2:8). ¹H NMR (DMSO-d₆); δ 3.77 (s, 3H), 3.79 (s, 3H), 6.12 (s, 2H), 6.23 (s, 2H), 7.50-7.59 (m, 2H), 7.77 (s, 4H), 7.81 (d, J=8.4 Hz, 2H), 8.09 (d, J=8.4 Hz, 2H), 8.50 (s, 1H), 8.83 (s, 1H). ¹³C NMR; δ 150.6, 148.8, 144.6, 144.5, 140.3, 138.5, 133.0, 131.4, 126.8, 126.2, 126.1, 126.0, 124.5, 123.2, 118.1, 115.8, 110.0, 60.6, 60.5. MS (m/z, rel.int.); 414 (M⁺, 60), 384 (10), 367 (50), 320 (100), 294 (10). High resolution mass calcd. for $C_{23}H_{22}N_6O_2$: 414.18042. Observed: 414.18122. (12, hydrochloride salt), mp 234-236° C. Anal. Calcd. for 12 ($C_{23}H_{22}N_6O_2$·3.0HCl·1.4H₂O·0.25EtOH): C % 50.35, H % 5.26, N % 14.99. Found: C % 50.57, H % 5.21, N % 14.69.

2-(4'-Amidinobiphenyl-4-yl)-5,6,7,8-tetrahydro-imidazo[1,2-a]pyridine-6-carboxamidine acetate salt (13a). The same procedure described for 7 was used starting with 11a. Yield 85%, mp 240-242° C. ¹H NMR (D₂O/DMSO-d₆); δ 2.03 (br s, 3×CH₃+3H), 2.86 (br s, 1H), 3.03 (br s, 1H), 4.16 (br s, 1H), 4.36 (br s, 1H), 7.57 (s, 1H), 7.75-7.77 (m, 2H), 7.85-7.91 (m, 6H). Anal. Calcd. for 13a ($C_{21}H_{22}N_6$·3.0AcOH·1.5H₂O): C % 57.31, H % 6.59, N % 14.86. Found: C % 57.27, H % 6.44, N % 14.77.

2-(4'-Amidinobiphenyl-4-yl)-imidazo[1,2-a]pyridine-6-carboxamidine acetate salt (14a). The same procedure described for 8a was used starting with 11a. Yield 81%, mp 243-246° C. ¹H NMR (D₂O/DMSO-d₆); δ 1.90 (s, 3×CH₃), 7.61-7.69 (m, 2H), 7.89-7.94 (m, 6H), 8.13 (s, 2H), 8.62 (s, 1H), 9.12 (s, 1H). MS (m/z, rel.int.); 354 (M⁺, 10), 321 (100), 311 (90), 296 (35). Anal. Calcd. for 14a ($C_{21}H_{18}N_6$·3.0AcOH·2.5H₂O): C % 55.95, H % 6.08, N % 14.50. Found: C % 55.76, H % 6.08, N % 14.71.

2-(3-Bromophenyl)-imidazo[1,2-a]pyridine-6-carbonitrile (9b). The same procedure described for 9a was used employing 3-Bromophenacyl bromide instead of 4-Bromophenacyl bromide. Yield 64%, mp 205-206.5° C. ¹H NMR (DMSO-d₆); δ 7.43-7.47 (m, 1H), 7.52-7.58 (m, 2H), 7.75-7.78 (m, 1H), 8.03 (s, 1H), 8.22 (s, 1H), 8.61-8.65 (m, 1H), 9.37 (s, 1H). ¹³C NMR; δ 144.6, 144.1, 135.2, 134.3, 130.9, 128.3, 125.1, 124.7, 122.2, 117.5, 116.9, 111.2, 97.2. MS (m/z, rel.int.); 298 (M⁺, 100), 161 (10). Anal. Calcd. for 9b ($C_{14}H_8BrN_3$): C % 56.40, H % 2.70. Found: C % 56.47, H % 2.73.

2-(4'-Cyanobiphenyl-3-yl)-imidazo[1,2-a]pyridine-6-carbonitrile (10b). The same procedure described for 4a was used starting with 9b. Yield 61%, mp 290-292° C. ¹H NMR (DMSO-d₆); δ 7.48-7.63 (m, 2H), 7.74-7.78 (m, 2H), 7.92-7.99 (m, 4H), 8.08 (d, J=7.8 Hz, 1H), 8.36 (s, 1H), 8.64 (s, 1H), 9.33 (s, 1H).

¹³C NMR; δ 146.7, 145.0, 144.9, 139.6, 135.0, 134.5, 133.6, 130.5, 128.4, 127.8, 126.9, 125.7, 125.2, 119.5, 118.2, 117.8, 111.7, 110.9, 97.9. MS (m/z, rel.int.); 320 (M⁺, 100), 297 (3), 217 (5), 190 (8), 160 (10). High resolution mass calcd. for $C_{21}H_{12}N_4$: 320.10620. Observed: 320.10619. Anal. Calcd. for 10b ($C_{21}H_{12}N_4$): C % 78.73, H % 3.78. Found: C % 78.48, H % 3.69.

N-Hydroxy-2-[4'-(N-hydroxyamidino)-biphenyl-3-yl]-imidazo[1,2-a]pyridine-6-carboxamidine (11b). The same procedure described for 5a was used starting with 10b. Yield 94%, mp 252-254° C. ¹H NMR (DMSO-d₆); δ 5.89 (s, 2H), 5.98 (s, 2H), 7.52-7.58 (m, 3H), 7.67 (d, J=8.1 Hz, 1H), 7.78 (d, J=8.7 Hz, 2H), 7.83 (d, J=8.7 Hz, 2H), 8.00 (d, J=7.8 Hz, 1H), 8.31 (s, 1H), 8.57 (s, 1H), 8.81 (s, 1H), 9.72 (s, 1H), 9.86 (s, 1H). ¹³C NMR; δ 150.5, 148.5, 144.6, 144.5, 140.3, 139.9, 134.3, 132.4, 129.3, 126.3, 125.9, 124.8, 123.9, 123.6, 123.2, 119.0, 115.8, 110.1. Anal. Calcd. for 1 1b ($C_{21}H_{18}N_6O_2$·2.0H₂O): C % 59.69, H % 5.21. Found: C % 59.90, H % 5.32.

2-(4'-Amidinobiphenyl-3-yl)-5,6,7,8-tetrahydro-imidazo[1,2-a]pyridine-6-carboxamidine acetate salt (13b). The same procedure described for 7 was used starting with 11b. Yield 65%, mp 236-238° C. $^1$H NMR (D$_2$O/DMSO-d$_6$); δ 1.90-2.17 (brs, 3×CH$_3$+3H), 2.79 (brs, 1H), 3.03 (brs, 1H), 4.11 (brs, 1H), 4.33 (br s, 1H), 7.48 (t, J=7.5 Hz, 1H), 7.57 (d, J=8.1 Hz, 1H), 7.71 (s, 1H), 7.79 (d, J=7.5 Hz, 1H), 7.90-7.96 (m, 4H), 8.09 (s, 1H). Anal. Calcd. for 13b (C$_{21}$H$_{22}$N$_6$.3.0AcOH-2.85H$_2$O-0.25EtOH): C % 54.92, H % 6.85, N % 13.98. Found: C % 54.91, H % 6.66, N % 13.64.

2-(4'-Amidinobiphenyl-3-yl)-imidazo[1,2-a]pyridine-6-carboxamidine acetate salt (14b). The same procedure described for 8a was used starting with 11b. Yield 57%, mp 233-235° C. $^1$H NMR (D$_2$O/DMSO-d$_6$); δ 1.87 (s, 3×CH$_3$), 7.55-7.69 (m, 4H), 7.72-7.92 (m, 4H), 8.05 (d, J=7.5 Hz, 1H), 8.33 (s, 1H), 8.56 (s, 1H), 9.03 (s, 1H). Anal. Calcd. for 14b (C$_{21}$H$_{18}$N$_6$.3.0AcOH-0.9H$_2$O): C % 58.87, H % 5.81, N % 15.26. Found: C % 58.60, H % 5.81, N % 15.60.

2-(3-Bromophenyl)-8-methyl-imidazo[1,2-a]pyridine-6-carbonitrile (9c). The same procedure described for 9b was used employing 6-Amino-5-methylnicotinonitrile instead of 6-Amino-nicotinonitrile. Yield 70%, mp 168-169.5° C. $^1$H NMR (DMSO-d$_6$); δ 2.55 (s, 3H), 7.36 (s, 1H), 7.43 (t, J=7.8 Hz, 1H), 7.55 (d, J=7.8 Hz, 1H), 8.01 (d, J=7.8 Hz, 1H), 8.20 (s, 1H), 8.57 (s, 1H), 9.20 (s, 1H). MS (m/z, rel.int.); 312 (M$^+$, 60), 175 (100), 135 (10). Anal. Calcd. for 9c (C$_{15}$H$_{10}$BrN$_3$): C % 57.71, H % 3.23. Found: C % 57.56, H % 3.15.

2-(4'-Cyanobiphenyl-3-yl)-8-methyl-imidazo[1,2-a]pyridine-6-carbonitrile (10c). The same procedure described for 4a was used starting with 9c. Yield 78%, mp 236-238° C. $^1$H NMR (DMSO-d$_6$); δ 2.56 (s, 3H), 7.34 (s, 1H), 7.60 (t, J=7.8 Hz, 1H), 7.73 (d, J=7.8 Hz, 1H), 7.97 (s, 4H), 8.10 (d, J=7.8 Hz, 1H), 8.34 (s, 1H), 8.64 (s, 1H), 9.21 (s, 1H). $^{13}$C NMR; δ 145.2, 144.7, 144.3, 138.7, 133.8, 132.8, 131.9, 129.6, 127.6, 127.5, 126.9, 126.1, 124.3, 122.8, 118.8, 117.1, 111.4, 110.1, 96.9, 16.3. Anal. Calcd. for 10c (C$_{22}$H$_{14}$N$_4$): C % 79.02, H % 4.22. Found: C % 78.81, H % 4.13.

N-Hydroxy-2-[4'-(N-hydroxyamidino)-biphenyl-3-yl]-8-methyl-imidazo[1,2-a]pyridine-6-carboxamidine (11 c). The same procedure described for 5a was used starting with 10c. Yield 97%, mp 193-195° C. $^1$H NMR (DMSO-d$_6$); δ 2.56 (s, 3H), 5.89 (s, 2H), 5.93 (s, 2H), 7.39 (s, 1H), 7.55 (t, J=7.8 Hz, 1H), 7.66 (d, J=7.8 Hz, 1H), 7.77 (d, J=9 Hz, 2H), 7.83 (d, J=9 Hz, 2H), 8.02 (d, J=7.8 Hz, 1H), 8.29 (s, 1H), 8.56 (s, 1H), 8.66 (s, 1H), 9.72 (s, 1H), 9.78 (s, 1H). $^{13}$C NMR; δ 150.4, 148.6, 145.1, 144.0, 140.3, 139.9, 134.5, 132.4, 129.3, 126.4, 125.8, 125.2, 124.8, 123.6, 121.8, 121.5, 118.9, 110.6, 16.7.

2-(4'-Amidinobiphenyl-3-yl)-8-methyl-imidazo[1,2-a]pyridine-6-carboxamidine acetate salt (14c). The same procedure described for 8a was used starting with 11c. Yield 81%, mp 237-239.5° C. $^1$H NMR (D$_2$O/DMSO-d$_6$); δ 1.75 (s, 3×CH$_3$), 2.54 (s, 3H), 7.43 (s, 1H), 7.62 (t, J=7.8 Hz, 1H), 7.74 (d, J=7.8 Hz, 1H), 7.95-7.99 (m, 4H), 8.11 (d, J=7.8 Hz, 1H), 8.38 (s, 1H), 8.72 (s, 1H), 9.01 (s, 1H). Anal. Calcd. for 14c (C$_{22}$H$_{20}$N$_6$.3.0AcOH-0.5H$_2$O): C % 60.31, H % 5.96, N % 15.07. Found: C % 60.33, H % 5.95, N % 15.12.

4-(6-Bromo-imidazo[1,2-a]pyridin-2-yl)-benzonitrile (15). The same procedure described for 3a was used employing 4-Cyanophenacyl bromide and 2-Amino-5-bromopyridine. Yield 62%, mp 218-219° C. (EtOH). $^1$H NMR (DMSO-d$_6$); δ 7.41 (d, J=8.7 Hz, 1H), 7.61 (d, J=8.7 Hz, 1H), 7.90 (d, J=8.4 Hz, 2H), 8.15 (d, J=8.4 Hz, 2H), 8.53 (s, 1H), 8.92 (s, 1H). $^{13}$C NMR; δ 143.5, 143.0, 137.9, 132.7, 128.5, 127.1, 126.1, 118.8, 117.0, 111.3, 110.0, 106.4. MS (m/z, rel.int.); 298 (M$^+$, 100). Anal. (C$_{14}$H$_8$BrN$_3$) C, H.

2,6-Bis(4-cyanophenyl)-imidazo[1,2-a]pyridine (16). The same procedure described for 4a was used starting with 15. Yield 69%, mp 292-294° C. (EtOH).
$^1$H NMR (DMSO-d$_6$); δ 7.70 (s, 2H), 7.88 (d, J=7.8 Hz, 2H), 7.94 (s, 4H), 8.17 (d, J=7.8 Hz, 2H), 8.55 (s, 1H), 9.02 (s, 1H). $^{13}$C NMR; δ 144.4, 143.2, 140.9, 138.0, 132.8, 132.6, 127.2, 126.1, 125.4, 125.0, 123.7, 118.8, 118.5, 117.0, 111.6, 110.2, 109.9. MS (m/z, rel.int.); 320 (M$^+$, 100), 293 (5), 191 (3), 179 (10), 160 (15). High resolution mass calcd. for C$_{21}$H$_{12}$N$_4$: 320.10620. Observed: 320.10640. Anal. (C$_{21}$H$_{12}$N$_4$) C, H.

2,6-Bis[4-(N-hydroxyamidino-phenyl)]-imidazo[1,2-a]pyridine (17). The same procedure described for 5a was used starting with 16. Yield 95%, mp 251-253° C. dec. $^1$H NMR (DMSO-d$_6$); δ 5.88 (s, 2H), 5.91 (s, 2H), 7.67 (s, 2H), 7.75-7.83 (m, 6H), 8.00 (d, J=8.4 Hz, 2H), 8.44 (s, 1H), 8.94 (s, 1H), 9.70 (s, 1H), 9.73 (s, 1H). $^{13}$C NMR; δ 150.6, 150.3, 144.4, 144.2, 136.8, 134.1, 132.55, 132.50, 126.0, 125.9, 125.7, 125.2, 124.8, 124.6, 124.0, 116.6, 109.8.

2,6-Bis[4-amidinophenyl)]-5,6,7,8-tetrahydro-imidazo[1,2-a]pyridine acetate salt (18). The same procedure described for 7 was used starting with 17. Yield 84%, mp 234-236° C. dec. $^1$H NMR (D$_2$O/DMSO-d$_6$); δ 1.75 (s, 3×CH$_3$), 2.15 (br s, 3H), 2.95 (br s, 2H), 4.09 (br s, 1H), 4.27 (br, 1H), 7.62 (m, 3H), 7.77-7.82 (m, 4H), 7.89-7.92 (m, 2H). Anal. (C$_{21}$H$_{22}$N$_6$.3.0AcOH-1.9H$_2$O)C, H, N.

(Free base of 18): mp 254-255° C. $^1$H NMR (D$_2$O/DMSO-d$_6$); δ 2.13-2.20 (m, 3H), 2.91 (m, 1H), 3.34 (br s, 1H), 4.03 (m, 1H), 4.27 (m, 1H), 7.62 (m, 3H), 7.77-7.82 (m, 4H), 7.89-7.92 (m, 2H). $^{13}$C NMR; δ 162.3, 144.2, 143.6, 138.7, 136.2, 126.8, 126.7, 123.4, 115.4, 99.4, 49.7, 27.6, 23.7. MS (m/z, rel.int., Fab./thioglycerol); 359 (M$^+$+1, 75), 324 (100), 291(5), 273 (15), 237 (20). High resolution mass calcd. for C$_{21}$H$_{23}$N$_6$: 359.19842. Observed: 359.19800.

2,6-Bis[4-amidinophenyl)]-imidazo[1,2-a]pyridine acetate salt (19). The same procedure described for 8a was used starting with 17. Yield 76%, mp 259-261° C. dec. $^1$H NMR (D$_2$O/DMSO-d$_6$); δ 1.97 (s, 3×CH$_3$), 7.67 (s, 2H), 7.77-7.88 (m, 6H), 8.07 (d, J=8.4 Hz, 2H), 8.48 (s, 1H), 8.94 (s, 1H). Anal. (C$_{21}$H$_{18}$N$_6$.3.0AcOH-1.9H$_2$O) C, H, N.

4-(6-Bromo-8-methyl-imidazo[1,2-a]pyridin-2-yl)-benzonitrile (20): The same procedure described for 3a was used employing 4-Cyanophenacyl bromide and 2-Amino-5-bromo-3-methylpyridine. Yield 71%, mp 209-210° C. $^1$H NMR (DMSO-d$_6$); δ 2.56 (s, 3H), 7.53 (s, 1H), 7.95 (d, J=8.1 Hz, 2H), 8.14 (d, J=8.1 Hz, 2H), 8.60 (s, 1H), 8.88 (s, 1H). $^{13}$C NMR; δ 143.3, 140.4, 133.3, 133.0, 128.1, 127.4, 127.0, 125.9, 119.2, 112.8, 111.2, 108.2, 16.7. MS (m/z, rel.int.); 312 (M$^+$, 10), 230 (100), 217 (60), 205 (50).

2,6-Bis(4-cyanophenyl)-8-methyl-imidazo[1,2-a]pyridine (21): The same procedure described for 4a was used starting with 20. Yield 73%, mp 283-285° C. $^1$H NMR (DMSO-d$_6$); δ 2.60 (s, 3H), 7.53 (s, 1H), 7.85-7.93 (m, 6H), 8.17 (d, J=8.4 Hz, 2H), 8.53 (s, 1H), 8.87 (s, 1H). $^{13}$C NMR; δ 144.9, 142.5, 141.1, 138.1, 132.6, 132.4, 127.0, 126.6, 126.0, 123.6, 123.3, 122.9, 118.6, 118.4, 111.9, 110.0, 109.7, 16.3. MS (m/z, rel.int.); 335 (M$^+$+1, 100), 310 (30), 279 (20), 234 (40).

2,6-Bis[4-(N-hydroxyamidino-phenyl)]-8-methyl-imidazo[1,2-a]pyridine (22). The same procedure described for 5a was used starting with 21. Yield 92%, mp>300° C. $^1$H NMR (DMSO-d$_6$); δ 2.60 (s, 3H), 6.22 (s, 2H), 6.40 (s, 2H), 7.51 (s, 1H), 7.76-7.90 (m, 6H), 8.03 (d, J=8.1 Hz, 2H), 8.44 (s, 1H), 8.80 (s, 1H), 9.93 (s, 2H). $^{13}$C NMR; δ 152.0, 151.2, 144.7, 143.5, 137.5, 134.8, 131.6, 131.1, 126.2, 126.1, 125.3, 124.6, 123.5, 121.9, 110.5, 16.8. MS (m/z, rel.int.); 401 (M$^+$+1, 75), 339 (20), 266 (10), 201 (100).

2,6-Bis[4-amidinophenyl)]-8-methyl-imidazo[1,2-a]pyridine acetate salt (23). The same procedure described for 8a was used starting with 22. Yield 81%, mp 241-243° C. dec. $^1$H NMR (D$_2$O/DMSO-d$_6$); δ 1.88 (s, 3×CH$_3$), 2.63 (s, 3H), 7.53 (s, 1H), 7.89-8.00 (m, 5H), 8.07-8.18 (m, 3H), 8.53 (s, 1H), 8.86 (s, 1H). Anal. Calcd. for 23 (C$_{22}$H$_{20}$N$_6$·3.0AcOH-1.7H$_2$O): C % 58.06, H % 6.16, N % 14.51. Found: C % 57.90, H % 5.93, N % 14.76.

Biological Results

The DNA binding studies and both the in vitro and in vivo antiprotozoan studies were performed as described by Ismail. M. A., et al., *J. Med. Chem.*, 46, 4761-4769 (2003), which is incorporated herein by reference in its entirety.

Table 1 contains the results from the DNA binding studies for the new diamidines and the in vitro results for the compounds tested against T. b. r. and P. f. The diamidines 8a, 8b, 14a, 14b and 14c all contain the unsaturated imidazo[1,2-a] pyridine unit and, consistent with the presence of the planer aromatic systems, show high DNA affinities as reflected by large ΔTm values (e.g., about 24 to >27). Changing the central ring from furanyl to 1,3-phenylene or 1,4-phenylene does not result in major differences in the observed DNA affinity. The diamidino tetrahydro imidazo[1,2-a]pyridine analogs 7, 13a, and 13b all exhibit somewhat lower ΔTm values (e.g., about 15 to about 21) than their unsaturated analogues. This diminution in DNA affinity is consistent with the presence of partially saturated rings, which deviate from planarity and thus do not form as effective stacking partners with the walls of the minor groove. Although the saturated analogs exhibit lower observed DNA affinity than their unsaturated counterparts, the affinities are relatively strong when compared to pentamidine (ΔTm=12). Due to much lower pK values, the N-hydroxy and N-methoxy potential prodrugs of amidines do not bind well to DNA. As a representative example of this class of compounds, compound 12 was evaluated and gave a ΔTm value of only 0.3.

The in vitro evaluation of these compounds (Table 1) shows promising results against both T. b. r. and P. f. Six of the eight diamidines gave IC$_{50}$ values of 63 nM or less against T. b. r. Two of the unsaturated analogues 8b and 14a gave quite low IC$_{50}$ values of 6 and 1 nM, respectively, against T. b. r. Six of the eight diamidines gave IC$_{50}$ values of 88 nM or less against P. f. The two most active compounds in vitro against P. f. are 8a and 13a. Both compounds gave an IC$_{50}$ value of 14 nM. One of these is a saturated analogue (13a) and the other is unsaturated (8a). As expected the prodrug molecules (5a, 6, 11a, 12) show essentially no in vitro activity due to the absence of the enzymes needed for bioconversion to the active diamidines.

The in vivo activities of these compounds in the STIB900 model for acute T. b. r. infection are shown in Table 2. In this model five of the diamidines (8a, 8b, 7, 14b, 14a) give 4/4 cures and two, 13a and 14c, give 3/4 cures on intraperitoneal dosage. The four prodrugs (5a, 6, 11a, 12), did not show high in vivo effectiveness on oral dosage. No attempts were made to optimize the formulation. Accordingly, these results might reflect the non-optimal absorption of the prodrug and not their in vivo activity against T. b. r. One of ordinary skill in the art would appreciate that optimization of the formulation could improve the oral bioavailability of the prodrug. The most effective prodrug compound, 6, gave only 2/4 cures at 100 mg/kg. This result is in contrast to the prodrug 111a and a number of the azafuramidine prodrug analogues that achieve 4/4 cures In sum, these biological results demonstrate that a new class of diary diamidines has been prepared which show strong DNA affinity and high in vitro activity against T. b. r. and P. f. The diamidines show excellent in vivo activity against T. b. r. on intraperitoneal dosage. The oral activity of the potential prodrugs is modest.

TABLE 1

DNA affinities and In Vitro Anti-protozoan Data.

| Code | L | B | R | A | ΔTm[a] Poly-(dA.dT)$_2$ | T.b.r.[b] IC$_{50}$ nM | P.f.[b] IC$_{50}$ nM |
|---|---|---|---|---|---|---|---|
| IIIa | na | na | na | Am | 25 | 4.5 | 15.5 |
| IIa | na | na | na | AmOMe | | 14.6K | 11.4K |
| 8a | 2,5-furanyl | unsat'd | H | Am | 26.2 | 63 | 14 |
| 5a | 2,5-furanyl | unsat'd | H | AmOH | | 2.2K | 1.6K |
| 8b | 2,5-furanyl | unsat'd | Me | Am | >27 | 6 | 88 |
| 7 | 2,5-furanyl | sat'd | H | Am | 15.6 | 52 | 1.2K |
| 6 | 2,5-furanyl | unsat'd | H | AmOMe | | 3K | 2.8K |
| 14b | 1,3-phenylene | unsat'd | H | Am | >27 | 22 | 107 |
| 14c | 1,3-phenylene | unsat'd | Me | Am | >27 | 49 | 86 |
| 13b | 1,3-phenylene | sat'd | H | Am | 19.1 | 226 | 86 |
| 14a | 1,4-phenylene | unsat'd | H | Am | 24.2 | 1 | 43 |
| 13a | 1,4-phenylene | sat'd | H | Am | 21.3 | 116 | 14 |
| 11a | 1,4-phenylene | unsat'd | H | AmOH | | >166K | 521 |
| 12 | 1,4-phenylene | unsat'd | H | AmOMe | 0.3 | 5.3K | 395 |
| 19 | na | unsat'd | H | BzAm | | 7 | 92 |
| 18 | na | sat'd | H | BzAm | | 14 | 85 |

[a]See Ismail. M. A., et al., J. Med. Chem., 46, 4761-4769 (2003);
[b]Average of duplicate determinations, see Ismail. M. A., et al., J. Med. Chem., 46, 4761-4769 (2003);
na = not applicable;
sat'd = saturated ring structure;
unsat'd = unsaturated ring structure;
K = 1,000;
IC$_{50}$ = the concentration that gives a 50% growth inhibition;
Am = (C=NH)NH$_2$;
AmOH = (C=NOH)NH$_2$; and
AmOMe = (C=NOMe)NH$_2$;
BzAm = benzamidine, e.g., (phenyl-(C=NH)NH$_2$).

TABLE 2

In vivo Anti-trypanosomal Activity of Imidazo[1,2-a]pyridines and 5,6,7,8-Tetrahydro-imidazo[1,2-a]pyridines Analogues in the STIB900 Mouse Model.[a,b]

| Compound | Dosage route[c] | Dosage (mg/kg) | Cures[d] | Survival (days)[e] |
|---|---|---|---|---|
| Pentamidine(I) | ip | 20 | 0/4 | 40.8 |
| Furamidine(IIa) | ip | 20 | 0/4 | 52.5 |
| IIIa | po | 100 | 4/4 | >60 |
| 8a | ip | 20 | 4/4 | >60 |
| 5a | po | 50 | 1/4 | >19.5 |
| 8b | ip | 20 | 4/4 | >60 |
| 7 | ip | 20 | 4/4 | >60 |
|  |  | 5 | 2/4 | >51 |
| 6 | po | 100 | 2/4 | >39.5 |
| 14b | ip | 20 | 4/4 | >60 |
| 14c | ip | 20 | 3/4 | >50 |
| 14a | ip | 20 | 4/4 | >60 |
| 13a | ip | 10 | 3/4 | >51.5 |
| 11a | po | 75 | 0/4 | 28 |
| 12 | po | 75 | 0/4 | 20 |

[a]See Ismail, M. A., et al., J. Med. Chem., 46, 4761-4769 (2003) for details of STIB900 model;
[b]IC$_{50}$ value for 13b did not meet criteria for entry into animal studies.
[c]ip = intraperitoneal; po = oral
[d]number of mice that survive and are parasite free for 60 days
[e]average days of survival; untreated control animals expire between day 7 and 8 post infection.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A compound of Formula (I):

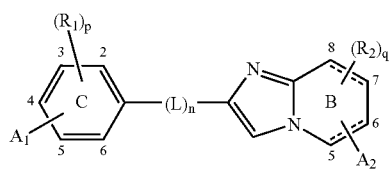
(I)

wherein:
 n is 1;
 p is an integer from 0 to 4;
 q is an integer from 0 to 3;
 $R_1$ and $R_2$ are each independently selected from the group consisting of alkyl, substituted alkyl, aryl, substituted aryl, halo, hydroxyl, alkoxyl, aryloxyl, and aralkyloxyl;
 L is selected from the group consisting of

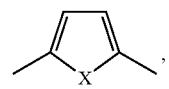 ,  , 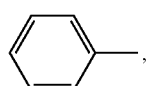 , and

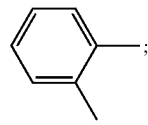;

wherein X is selected from the group consisting of O, S, and $NR_3$, and wherein $R_3$ is selected from the group consisting of H, alkyl, substituted alkyl, and alkoxyl;
 B is selected from the group consisting of a saturated ring structure, a partially saturated ring structure, and an unsaturated ring structure;
 $A_1$ and $A_2$ are each independently:

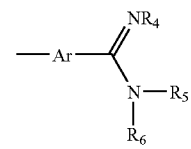

wherein:
 Ar is selected from the group consisting of an aryl group and a substituted aryl group and can be present or absent;
 $R_4$, $R_5$, and $R_6$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
 $R_4$ and $R_5$ together represent a $C_2$ to $C_{10}$ alkyl, hydroxyalkyl, or alkylene;
or a pharmaceutically acceptable salt thereof.

2. The compound of claim 1, wherein:
 L is

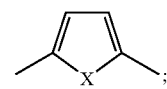;

X is O; and
 $A_1$ and $A_2$ each comprise

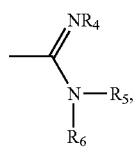

wherein $A_1$ is in the 4-position of ring C and $A_2$ is in the 6-position of ring B.

3. The compound of claim 1, wherein:

L is selected from the group consisting of:

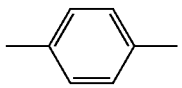 and 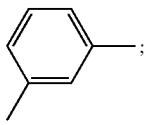;

$A_1$ and $A_2$ each comprise

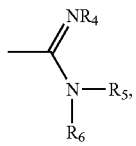

wherein $A_1$ is in the 4-position of ring C and $A_2$ is in the 6-position of ring B.

4. A compound of the formula:

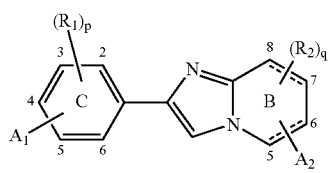

wherein:
- p is an integer from 0 to 4;
- q is an integer from 0 to 3;
- $R_1$ and $R_2$ are each independently selected from the group consisting of alkyl, substituted alkyl, aryl, substituted aryl, halo, hydroxyl, alkoxyl, aryloxyl, and aralkyloxyl;
- B is selected from the group consisting of a saturated ring structure, a partially saturated ring structure, and an unsaturated ring structure;
- $A_1$ is in the 4-position of ring C and comprises

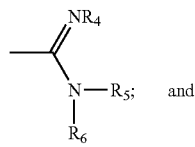 and $A_2$ is in the 6-position of ring B and comprises

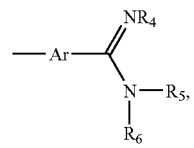

wherein:
- Ar is selected from the group consisting of an aryl group and a substituted aryl group;
- $R_4$, $R_5$, and $R_6$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
- $R_4$ and $R_5$ together represent a $C_2$ to $C_{10}$ alkyl, hydroxyalkyl, or alkylene;

or a pharmaceutically acceptable salt thereof.

5. The compound of claim 1, wherein the compound is selected from the group consisting of:
- N-Hydroxy-2-{5-[4-(N-hydroxyamidino)-phenyl]-furan-2-yl}-imidazo[1,2-a]pyridine-6-carboxamidine;
- N-Methoxy-2-{5-[4-(N-methoxyamidino)-phenyl]-furan-2-yl}-imidazo[1,2-a]pyridine-6-carboxamidine;
- 2-[5-(4-Amidinophenyl)-furan-2-yl]-5,6,7,8-tetrahydro-imidazo[1,2-a]pyridine-6-carboxamidine;
- 2-[5-(4-Amidinophenyl)-furan-2-yl]-imidazo[1,2-a]pyridine-6-carboxamidine;
- N-Hydroxy-2-{5-[4-(N-hydroxyamidino)-phenyl]-furan-2-yl}-8-methyl-imidazo[1,2-a]pyridine-6-carboxamidine;
- 2-[5-(4-Amidinophenyl)-furan-2-yl]-8-methyl-imidazo[1,2-a]pyridine-6-carboxamidine;
- N-Hydroxy-2-[4'-(N-hydroxyamidino)-biphenyl-4-yl]-imidazo[1,2-a]pyridine-6-carboxamidine;
- N-Methoxy-2-[4'-(N-methoxyamidino)-biphenyl-4-yl]-imidazo[1,2-a]pyridine-6-carboxamidine;
- 2-(4'-Amidinobiphenyl-4-yl)-5,6,7,8-tetrahydro-imidazo[1,2-a]pyridine-6-carboxamidine;
- 2-(4'-Amidinobiphenyl-4-yl)-imidazo[1,2-a]pyridine-6-carboxamidine;
- N-Hydroxy-2-[4'-(N-hydroxyamidino)-biphenyl-3-yl]-imidazo[1,2-a]pyridine-6-carboxamidine;
- 2-(4'-Amidinobiphenyl-3-yl)-5,6,7,8-tetrahydro-imidazo[1,2-a]pyridine-6-carboxamidine;
- 2-(4'-Amidinobiphenyl-3-yl)-imidazo[1,2-a]pyridine-6-carboxamidine;
- N-Hydroxy-2-[4'-(N-hydroxyamidino)-biphenyl-3-yl]-8-methyl-imidazo[1,2-a]pyridine-6-carboxamidine; and
- 2-(4'-Amidinobiphenyl-3-yl)-8-methyl-imidazo[1,2-a]pyridine-6-carboxamidine;

or a pharmaceutically acceptable salt thereof.

6. The compound of claim 1, wheerein the compound comprises a pharmaceutically acceptable salt.

7. The compound of claim 6, wherein the pharmaceutically acceptable salt is selected from the group consisting of a hydrochloride salt and an acetate salt.

8. A pharmaceutical formulation comprising:
(a) a compound of claim 1; and
(b) a pharmaceutically acceptable carrier.

9. A method for treating a microbial infection in a subject in need of treatment thereof, the method comprising administering to the subject an effective amount of a compound of Formula (I):

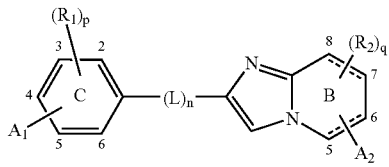

wherein:
- n is 1;
- p is an integer from 0 to 4;
- q is an integer from 0 to 3;

$R_1$ and $R_2$ are each independently selected from the group consisting of alkyl, substituted alkyl, aryl, substituted aryl, halo, hydroxyl, alkoxyl, aryloxyl, and aralkyloxyl;

L is selected from the group consisting of

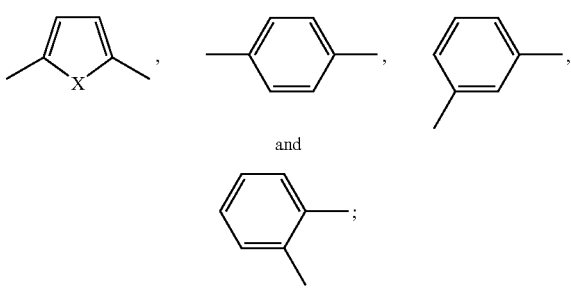

and

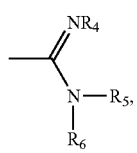

wherein X is selected from the group consisting of O, S, and $NR_3$, and wherein $R_3$ is selected from the group consisting of H, alkyl, substituted alkyl, or alkoxyl;

B is selected from the group consisting of a saturated ring structure, a partially saturated ring structure, and an unsaturated ring structure;

$A_1$ and $A_2$ are each independently:

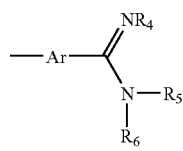

wherein:

Ar is selected from the group consisting of an aryl group and a substituted aryl group and can be present or absent;

$R_4$, $R_5$, and $R_6$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_4$ and $R_5$ together represent a $C_2$ to $C_{10}$ alkyl, hydroxyalkyl, or alkylene;

or a pharmaceutically acceptable salt thereof.

10. The method of claim 9, wherein:

L is

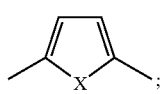

X is O; and $A_1$ and $A_2$ each comprise

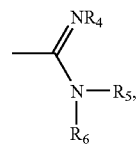

wherein $A_1$ is in the 4-position of ring C and $A_2$ is in the 6-position of ring B.

11. The method of claim 9, wherein:

L is selected from the group consisting of:

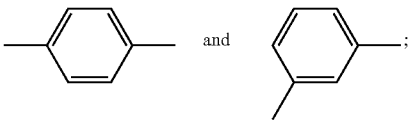

$A_1$ and $A_2$ each comprise

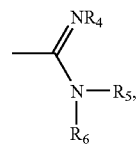

wherein $A_1$ is in the 4-position of ring C and $A_2$ is in the 6-position of ring B.

12. A method for treating a microbial infection in a subject in need of treatment thereof, the method comprising administering to the subject an effective amount of a compound of the formula:

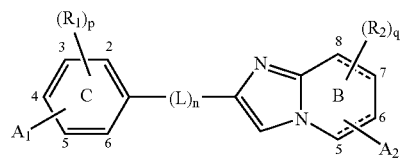

wherein:

p is an integer from 0 to 4;

q is an integer from 0 to 3;

$R_1$ and $R_2$ are each independently selected from the group consisting of alkyl, substituted alkyl, aryl, substituted aryl, halo, hydroxyl, alkoxyl, aryloxyl, and aralkyloxyl;

B is selected from the group consisting of a saturated ring structure, a partially saturated ring structure, and an unsaturated ring structure;

$A_1$ is in the 4-position of ring C and comprises

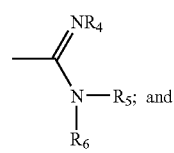

$A_2$ is in the 6-position of ring B and comprises

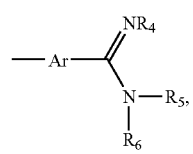

wherein:
Ar is selected from the group consisting of an aryl group and a substituted aryl group;
$R_4$, $R_5$, and $R_6$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_4$ and $R_5$ together represent a $C_2$ to $C_{10}$ alkyl, hydroxyalkyl, or alkylene;
or a pharmaceutically acceptable salt thereof.

13. The method of claim 9, wherein the compound of Formula (I) is selected from the group consisting of:
N-Hydroxy-2-{5-[4-(N-hydroxyamidino)-phenyl]-furan-2-yl}-imidazo[1,2-a]pyridine-6-carboxamidine;
N-Methoxy-2-{5-[4-(N-methoxyamidino)-phenyl]-furan-2-yl}-imidazo[1,2-a]pyridine-6-carboxamidine;
2-[5-(4-Amidinophenyl)-furan-2-yl]-5,6,7,8-tetrahydro-imidazo[1,2-a]pyridine-6-carboxamidine;
2-[5-(4-Amidinophenyl)-furan-2-yl]-imidazo[1,2-a]pyridine-6-carboxamidine;
N-Hydroxy-2-{5-[4-(N-hydroxyamidino)-phenyl]-furan-2-yl}-8-methyl-imidazo[1,2-a]pyridine-6-carboxamidine;
2-[5-(4-Amidinophenyl)-furan-2-yl]-8-methyl-imidazo[1,2-a]pyridine-6-carboxamidine;
N-Hydroxy-2-[4'-(N-hydroxyamidino)-biphenyl-4-yl]-imidazo[1,2-a]pyridine-6-carboxamidine;
N-Methoxy-2-[4'-(N-methoxyamidino)-biphenyl-4-yl]-imidazo[1,2-a]pyridine-6-carboxamidine;
2-(4'-Amidinobiphenyl-4-yl)-5,6,7,8-tetrahydro-imidazo[1,2-a]pyridine-6-carboxamidine;
2-(4'-Amidinobiphenyl-4-yl)-imidazo[1,2-a]pyridine-6-carboxamidine;
N-Hydroxy-2-[4'-(N-hydroxyamidino)-biphenyl-3-yl]-imidazo[1,2-a]pyridine-6-carboxamidine;
2-(4'-Amidinobiphenyl-3-yl)-5,6,7,8-tetrahydro-imidazo[1,2-a]pyridine-6-carboxamidine;
2-(4'-Amidinobiphenyl-3-yl)-imidazo[1,2-a]pyridine-6-carboxamidine;
N-Hydroxy-2-[4'-(N-hydroxyamidino)-biphenyl-3-yl]-8-methyl-imidazo[1,2-a]pyridine-6-carboxamidine; and
2-(4'-Amidinobiphenyl-3-yl)-8-methyl-imidazo[1,2-a]pyridine-6-carboxamidine;
or a pharmaceutically acceptable salt thereof.

14. The method of claim 9, wherein the microbial infection is selected from one of a *Trypanosoma brucei rhodesiense* infection and a *Plasmodium falciparum* infection.

15. The method of claim 9, wherein the compound of Formula I is administered in the form of a pharmaceutically acceptable salt.

16. The method of claim 15, wherein the pharmaceutically acceptable salt is selected from the group consisting of a hydrochloride salt and an acetate salt.

17. A method for preparing a compound of Formula (I):

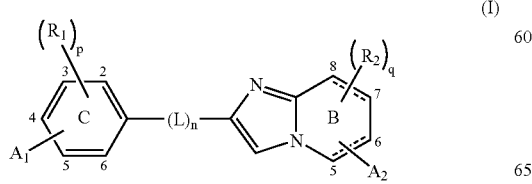

(I)

wherein:
n is an integer from 0 to 1;
p is an integer from 0 to 4;
q is an integer from 0 to 3;
$R_1$ and $R_2$ are each independently selected from the group consisting of alkyl, substituted alkyl, aryl, substituted aryl, halo, hydroxyl, alkoxyl, aryloxyl, and aralkyloxyl;
L is selected from the group consisting of

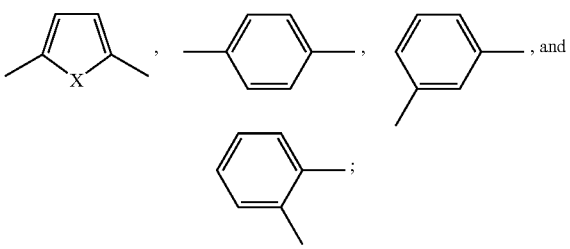

wherein X is selected from the group consisting of O, S, and $NR_3$, and wherein $R_3$ is selected from the group consisting of H, alkyl, substituted alkyl, and alkoxyl;
B is selected from the group consisting of a saturated ring structure, a partially saturated ring structure, and an unsaturated ring structure;
$A_1$ and $A_2$ are each independently:

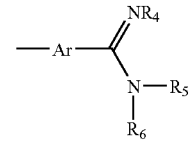

wherein:
Ar is selected from the group consisting of an aryl group and a substituted aryl group and can be present or absent;
$R_4$, $R_5$, and $R_6$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_4$ and $R_5$ together represent a $C_2$ to $C_{10}$ alkyl, hydroxyalkyl, or alkylene;
or a pharmaceutically acceptable salt thereof,
the method comprising:
(a) reacting an aryl-substituted alkylketone halide with an aminopyridine to form an aryl-substituted imidazo[1,2-a]pyridine;
(b) mixing the aryl-substituted imidazo[1,2-a]pyridine and a first catalyst in the presence of a base to form a first reaction mixture;
(c) adding a cyanophenyl-boronic acid to the first reaction mixture to form a cyanophenyl derivative of the aryl-substituted imidazo[1,2-a]pyridine;
(d) mixing an alkali metal alkoxide and a reducing agent to form a second reaction mixture; and
(e) adding the second reaction mixture to the cyanophenyl derivative of the aryl-substituted imidazo[1,2-a]pyridine to form an imidazo[1,2-a]pyridine bis-amidoxime of Formula (I).

18. The method of claim 17, wherein the aryl-substituted alkylketone halide is selected from the group consisting of 2-Bromo-1-(5-bromo-furan-2-yl)-ethanone, 3-Bromophenacyl bromide, 4-Bromophenacyl bromide, and 4-Cyanophenacyl bromide.

19. The method of claim 17, wherein the amino-pyridine is selected from the group consisting of an amino-cyanopyridine, an alkylated amino-cyanopyridine, and an amino-halopyridine.

20. The method of claim 19, wherein the amino-cyanopyridine comprises 6-Amino-3-cyanopyridine.

21. The method of claim 19, wherein the alkylated amino-cyanopyridine comprises 6-Amino-5-methyl-3-cyanopyridine.

22. The method of claim 19, wherein the amino-halopyridine is selected from the group consisting of 2-Amino-5-bromopyridine and 2-Amino-5-bromo-3-methylpyridine.

23. The method of claim 17, wherein the first catalyst comprises tetrakis(triphenylphosphine)palladium.

24. The method of claim 17, wherein the base comprises a carbonate salt.

25. The method of claim 17, wherein the cyanophenylboronic acid is selected from the group consisting of 4-Cyanophenyl boronic acid and 3-Cyanophenylboronic acid.

26. The method of claim 17, wherein the alkali metal alkoxide comprises potassium-t-butoxide.

27. The method of claim 17, wherein the reducing agent comprises hydroxylamine hydrochloride.

28. The method of claim 17, comprising reacting the imidazo[1,2-a]pyridine bis-amidoxime with an alkylating agent to form an imidazo[1,2-a]pyridine bis-O-alkylamidoxime of Formula (I).

29. The method of claim 28, wherein the alkylating agent comprises a dialkyl sulfate.

30. The method of claim 17 comprising:
(a) reacting the imidazo[1,2-a]pyridine bis-amidoxime with an acylating agent in a first protic solvent to form an acylated product;
(b) adding a second catalyst to the acylated product in a second protic solvent to form a third reaction mixture; and
(c) exposing the third reaction mixture to hydrogen under pressure for a period of time to form:
(i) a saturated imidazo[1,2-a]pyridine diamidine of Formula (I); and
(ii) an unsaturated imidazo[1,2-a]pyridine diamidine of Formula (I).

31. The method of claim 30, wherein the acylating agent comprises acetic anhydride.

32. The method of claim 30, wherein the second catalyst comprises a palladium on carbon catalyst.

33. The method of claim 30, wherein the first protic solvent comprises an acetic acid.

34. The method of claim 30, wherein the second protic solvent is selected from the group consisting of an acetic acid and an alkyl alcohol.

35. The method of claim 30, comprising exposing the third reaction mixture to hydrogen under pressure for a period of time in a mixture of an alkyl alcohol and an alkyl ester to form an unsaturated imidazo[1,2-a]pyridine diamidine of Formula (I).

36. The method of claim 35, wherein the alkyl ester comprises ethyl acetate.

37. The method of claim 4, wherein the compound is selected from the group consisting of:
2,6-Bis[4-(N-hydroxyamidino-phenyl)]-imidazo[1,2-a]pyridine;
2,6-Bis[4-amidinophenyl)]-5,6,7,8-tetrahydro-imidazo[1,2-a]pyridine;
2,6-Bis[amidinophenyl)]-imidazo[1,2-a]pyridine;
2,6-Bis[4-(N-hydroxyamidino-phenyl)]-8-methyl-imidazo[1,2-a]pyridine;
and
2,6-Bis[4-amidinophenyl)]-8-methyl-imidazo[1,2-a]pyridine;
or a pharmaceutically acceptable salt thereof.

38. A pharmaceutical formulation comprising:
(a) a compound of claim 4; and
(b) a pharmaceutically acceptable carrier.

39. The method of claim 12, wherein the compound is selected from the group consisting of:
2,6-Bis[4-(N-hydroxyamidino-phenyl)]-imidazo[1,2-a]pyridine;
2,6-Bis[4-amidinophenyl)]-5,6,7,8-tetrahydro-imidazo[1,2-a]pyridine;
2,6-Bis[amidinophenyl)]-imidazo[1,2-a]pyridine;
2,6-Bis[4-(N-hydroxyamidino-phenyl)]-8-methyl-imidazo[1,2-a]pyridine;
and
2,6-Bis[4-amidinophenyl)]-8-methyl-imidazo[1,2-a]pyridine;
or a pharmaceutically acceptable salt thereof.

40. The method of claim 12, wherein the microbial infection is selected from one of a *Trypanosoma brucei rhodesiense* infection and a *Plasmodium falciparum* infection.

* * * * *